(12) United States Patent
Boyden et al.

(10) Patent No.: US 9,720,167 B2
(45) Date of Patent: Aug. 1, 2017

(54) BIODEGRADABLE OPTICAL FIBERS AND METHODS OF USE THEREOF

(71) Applicant: Elwha LLC, Bellevue, WA (US)

(72) Inventors: Edward S. Boyden, Chestnut Hill, MA (US); Gregory J. Della Rocca, Columbia, MO (US); Colin P. Derdeyn, St. Louis, MO (US); Roderick A. Hyde, Redmond, WA (US); Muriel Y. Ishikawa, Livermore, CA (US); Jordin T. Kare, San Jose, CA (US); Eric C. Leuthardt, St. Louis, MO (US); Nathan P. Myhrvold, Medina, WA (US); Paul Santiago, St. Louis, MO (US); Todd J. Stewart, St. Louis, MO (US); Clarence T. Tegreene, Mercer Island, WA (US); Lowell L. Wood, Jr., Bellevue, WA (US); Victoria Y. H. Wood, Livermore, CA (US); Stephen L. Malaska, Redmond, WA (US)

(73) Assignee: Elwha LLC, Bellevue, WA (US)

( * ) Notice: Subject to any disclaimer, the term of this patent is extended or adjusted under 35 U.S.C. 154(b) by 146 days.

(21) Appl. No.: 14/627,835

(22) Filed: Feb. 20, 2015

(65) Prior Publication Data

US 2016/0245990 A1 Aug. 25, 2016

(51) Int. Cl.
*G02B 6/02* (2006.01)
*A61N 5/06* (2006.01)
(Continued)

(52) U.S. Cl.
CPC ....... *G02B 6/02033* (2013.01); *A61N 5/0601* (2013.01); *A61B 2017/00004* (2013.01);
(Continued)

(58) Field of Classification Search
CPC .. A61B 2017/00004; A61B 2018/2222; A61B 2018/2244; G02B 6/02033;
(Continued)

(56) References Cited

U.S. PATENT DOCUMENTS 6,400,880 B1   6/2002   Hebert et al.
6,835,679 B2  12/2004   Bilanin et al.
(Continued)

FOREIGN PATENT DOCUMENTS

WO     WO 0185637 A2 * 11/2001   ........... A61B 5/1455

OTHER PUBLICATIONS

Bernstein et al.; "Optogenetic tools for analyzing the neural circuits of behavior"; Trends in Cognitive Sciences; Dec. 2011; pp. 592-600; vol. 15, No. 12; Elsevier Ltd.
(Continued)

*Primary Examiner* — Gary Jackson
*Assistant Examiner* — Scott T Luan

(57) ABSTRACT

A device and methods of use thereof are disclosed herein for a biodegradable optical fiber and a method of producing a device including a biodegradable optical fiber. A device is disclosed that includes: a biodegradable optical fiber including; a biodegradable optically functional inner fiber including an optically-transmitting cladding in contact with and surrounding an optically-transmitting core, wherein the inner fiber is biodegradable on a first time scale; and an outer layer in contact with and surrounding the optically-transmitting cladding, wherein the outer layer is biodegradable on a controllably-defined delayed time scale, and the controllably-defined delayed time scale is of greater duration than the first time scale.

9 Claims, 9 Drawing Sheets

(51) Int. Cl.
G02B 6/036 (2006.01)
A61B 17/00 (2006.01)
A61B 18/22 (2006.01)

(52) U.S. Cl.
CPC ........... A61B 2018/2222 (2013.01); A61B 2018/2244 (2013.01); A61N 2005/0602 (2013.01); A61N 2005/063 (2013.01); A61N 2005/0662 (2013.01)

(58) Field of Classification Search
CPC .......... A61N 5/0601; A61N 2005/0602; A61N 2005/063; A61N 2005/0662
See application file for complete search history.

(56) References Cited

U.S. PATENT DOCUMENTS

| | | | |
|---|---|---|---|
| 8,369,673 B2 | 2/2013 | Hawkes et al. | |
| 8,553,223 B2 | 10/2013 | McKenna | |
| 2010/0249912 A1* | 9/2010 | Gibbons, Jr. | A61L 31/148 623/1.38 |
| 2015/0073513 A1* | 3/2015 | Redmond | A61N 5/062 607/88 |

OTHER PUBLICATIONS

Dupuis et al.; "Prospective for biodegradable microstructured optical fibers"; Optics Letters; Jan. 15, 2007; pp. 109-111; vol. 32, No. 2; Optical Society of America.

Ghanbarzadeh et al.; *Biodegradable Polymers, Biodegradation—Life of Science*, Dr. Rolando Chamy (Ed.); ISBN: 978-953-51-1154-2; published Jun. 13, 2014; Chapter 6; pp. 1-46; InTech, DOI: 10.5772/56230; available from: http://www.intechopen.com/books/biodegradation-life-of-science/biodegradable-polymers.

Kreeger et al.; "Evaluation of Pediatric Near-Infrared Cerebral Oximeter for Cardiac Disease"; Ann Thorac Surg; May 11, 2012; pp. 1527-1533; vol. 94; The Society of Thoracic Surgeons; Elsevier Inc.

Lasermate Group, Inc.; "UV, Blue, Green, Red & Infrared Laser Modules"; Dec. 9, 2014; product information; pp. 1-4; located at http://www.lasermate.com/GRImodule.htm.

"List of laser types"; from Wikipedia, the free encyclopedia; pp. 1-8; Dec. 2, 2014; located at http://en.wikipedia.org/wiki/List_of_laser_types.

Mader, Karsten; "Resomer®—Biodegradable Polymers for Sutures, Medical Devices, Drug Delivery Systems and Tissue Engineering"; Nov. 25, 2014; product information; pp. 1-6; located at http://www.sigmaaldrich.com/technical-documents/articles/material-matters/resomer-biodegradable-polymers.html; Sigma-Aldrich Col., LLC.

Mendez, Alexis; "Medical Applications of Fiber-Optics: Optical fiber sees growth as medical sensors"; Laser Focus World; Jan. 1, 2011; pp. 1-17; located at http://www.laserfocusworld.com/articles/2011/01/medical-applications-of-fiber-optics-optical-fiber-sees-growth-as-medical-sensors.html.

Plastic Optics, Division of Align Optics; "Properties of Optical Plastic Materials"; printed on Jan. 12, 2015; product information; pp. 1-2; located at http://www.plasticoptics.com/optical-plastic-materials.html.

Sikka et al.; "Melanopsin mediates light-dependent relaxation in blood vessels"; PNAS; Dec. 16, 2014; pp. 17977-17982; vol. 111, No. 50.

* cited by examiner

BIODEGRADABLE OPTICAL FIBERS AND METHODS OF USE THEREOF

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

A device and methods of use thereof are disclosed herein for a biodegradable optical fiber and a method of producing a device including a biodegradable optical fiber.

A device is disclosed that includes: a biodegradable optical fiber including: a biodegradable optically functional inner fiber including an optically-transmitting cladding in contact with and surrounding an optically-transmitting core, wherein the inner fiber is biodegradable on a first time scale; and an outer layer in contact with and surrounding the optically-transmitting cladding, wherein the outer layer is biodegradable on a controllably-defined delayed time scale, and the controllably-defined delayed time scale is of greater duration than the first time scale.

In some aspects, the outer layer may comprise a single material. The outer layer may be less optically transmissive than the cladding or the core. The outer layer may have an index of refraction greater than an index of refraction of the cladding. A composition of the outer layer may determine rate of biodegradation at the controllably-defined delayed time scale of the outer layer. The thickness of the outer layer may determine rate of biodegradation at the controllably-defined delayed time scale of the outer layer. The optically functional inner fiber may be biodegradable on a substantially instantaneous time scale.

In some aspects, the outer layer comprises a photodegradable material. The photodegradable material may be responsive to defined wavelengths of light. The defined wavelengths of light may be propagated axially along the photodegradable material of the outer layer. The defined wavelengths of light may be one or more of UV light, near UV light, and visible light.

A method of producing a device including a biodegradable optical fiber is disclosed that includes: contacting and surrounding an optically-transmitting core with an optically-transmitting cladding to form a biodegradable optically functional inner fiber, wherein the inner fiber is biodegradable on a first time scale; and contacting and surrounding the optically-transmitting cladding of the optically functional inner fiber with an outer layer, and the outer layer is biodegradable on a controllably-defined delayed time scale, wherein the controllably-defined delayed time scale is of greater duration than the first time scale. In some aspects, the outer layer may comprise a single material. The outer layer may be less optically transmissive than the cladding or the core. The outer layer may have an index of refraction greater than that of the cladding. The contacting and the surrounding the optically-transmitting cladding of the optically functional inner fiber with the outer layer may be performed at a later time than the formation of the inner fiber.

In some aspects, the contacting of the optically functional inner fiber with the outer layer may comprise applying the outer layer as a coating over the inner fiber. The contacting and the surrounding the optically-transmitting cladding of the optically functional inner fiber with the outer layer may be performed by spraying, dipping, or painting. A composition of the non-optically-transmitting outer layer may determine rate of biodegradation at the controllably-defined delayed time scale of the outer layer. The thickness of the non-optically-transmitting outer layer may determine rate of biodegradation at the controllably-defined delayed time scale of the outer layer. The optically functional inner fiber may be biodegradable on a substantially instantaneous time scale. In some aspects, the non-optically-transmitting outer layer may comprise a photodegradable material. The photodegradable material may be responsive to defined wavelengths of light. The defined wavelengths of light may be propagated axially along the photodegradable material of the outer layer.

A device is disclosed that includes: a photodegradable optical fiber including: a photodegradable optically functional inner fiber including an optically-transmitting cladding in contact with and surrounding an optically-transmitting core, wherein the inner fiber is photodegradable to yield biodegradable products. In some aspects, an outer layer in contact with and surrounding the optically-transmitting cladding, wherein the outer layer is biodegradable on a controllably-defined delayed time scale to yield biodegradable products, and the controllably-defined delayed time scale is longer than a time scale of photodegradation of the inner fiber. The outer layer may comprise a single material. The outer layer may be less optically transmissive than the cladding or the core. The outer layer may have an index of refraction greater than an index of refraction of the cladding. In some aspects, an outer layer may be in contact with and surrounding the optically-transmitting cladding, wherein the outer layer is photodegradable. The photodegradable outer layer may be responsive to defined wavelengths of light. The outer layer may comprise a single material. The outer layer may be optically transmissive for the defined wavelengths of light.

In some aspects, the photodegradable material may be responsive to defined wavelengths of light. The defined wavelengths of light may be propagated axially along a defined fraction of the photodegradable material of the inner fiber. The inner fiber may be substantially non-photodegradable in response to a second wavelength of light, the second wavelength of light propagated axially along the inner fiber and different from the defined wavelengths of light. In some aspects, the defined wavelengths of light may be one or more of UV light, near UV light, and visible light. A composition of the outer layer may determine rate of biodegradation at the controllably-defined delayed time scale of the outer layer. The thickness of the outer layer may determine rate of biodegradation at the controllably-defined delayed time scale of the outer layer. The optically functional inner fiber may be photodegradable on a substantially instantaneous time scale.

A method of producing a device including a photodegradable optical fiber is disclosed that includes: contacting and surrounding an optically-transmitting core with an optically-transmitting cladding to form a photodegradable optically functional inner fiber. In some aspects, the method may include contacting and surrounding the optically-transmitting cladding of the photodegradable optically functional inner fiber with an outer layer, wherein the outer layer is photodegradable to yield biodegradable products. The outer layer may comprise a single material. The outer layer may be less optically transmissive than the cladding or the core. The outer layer may have an index of refraction greater than that of the cladding. In some aspects, the contacting and the surrounding the optically-transmitting cladding of the optically functional inner fiber with the outer layer may be performed at a later time than the formation of the inner fiber.

In some aspects, the contacting of the optically functional inner fiber with the outer layer comprises applying the outer layer as a coating over the inner fiber. The contacting and the surrounding the optically-transmitting cladding of the optically functional inner fiber with the outer layer may be performed by spraying, dipping, or painting. In some aspects, the photodegradable material may be responsive to defined wavelengths of light. The defined wavelengths of light may be propagated axially along the photodegradable material of the inner fiber. The inner fiber may be substantially non-photodegradable in response to a second wavelength of light, the second wavelength of light propagated axially along the inner fiber and different from the defined wavelengths of light.

In some aspects, a composition of the outer layer may determine rate of biodegradation at the controllably-defined delayed time scale of the outer layer. The thickness of the outer layer may determine rate of biodegradation at the controllably-defined delayed time scale of the outer layer. The optically functional inner fiber may be photodegradable on a substantially instantaneous time scale.

A method for diagnostic assay in a vertebrate subject is disclosed that includes: inserting within a vertebrate subject a device comprising a photodegradable optical fiber including: a photodegradable optically functional inner fiber including an optically-transmitting cladding in contact with and surrounding an optically-transmitting core, wherein the inner fiber is configured to photodegrade to yield biodegradable products; wherein the device is configure to determine a biological parameter while inserted within the vertebrate subject.

A method for treating a disease or condition in a vertebrate subject is disclosed that includes: inserting within a vertebrate subject a device comprising a photodegradable optical fiber including: a photodegradable optically functional inner fiber including an optically-transmitting cladding in contact with and surrounding an optically-transmitting core, wherein the inner fiber is configured to photodegrade to yield biodegradable products in response to a first defined wavelength of light; wherein the device is configured to administer a second defined wavelength of electromagnetic radiation while inserted within the vertebrate subject. The device may be configured to administer the second defined wavelength of electromagnetic radiation in combination with administration of a pharmaceutical composition. The first defined wavelength of electromagnetic radiation may be configured to photodegrade the photodegradable optical fiber to yield biodegradable products. The second defined wavelength of electromagnetic radiation may be configured to have a therapeutic effect on the vertebrate subject.

In some aspects, the method may further include administering the second defined wavelength of electromagnetic radiation from the device while inserted within the vertebrate subject. In some aspects, the method of claim 56, comprising administering the first defined wavelength of electromagnetic radiation to photodegrade the photodegradable optical fiber to yield biodegradable products. The method may further include inserting the device comprising the photodegradable optical fiber within a blood vessel or lymph vessel of the vertebrate subject. The method may further include administering the second defined wavelength of electromagnetic radiation to induce relaxation or dilation of a blood vessel wall or a lymph vessel wall. The method may further include administering the second defined wavelength of 440 to 470 nanometers from the device while inserted within the vertebrate subject.

A method for treating a disease or condition in a vertebrate subject is disclosed that includes: inserting within a vertebrate subject a device comprising a biodegradable optical fiber including: a biodegradable optically functional inner fiber including an optically-transmitting cladding in contact with and surrounding an optically-transmitting core, wherein the inner fiber is configured to biodegrade on a first time scale; and an outer layer in contact with and surrounding the optically-transmitting cladding, wherein the outer layer is biodegradable on a controllably-defined delayed time scale, and the controllably-defined delayed time scale is of greater duration than the first time scale. In some aspects, the device may be configured to administer a defined wavelength of electromagnetic radiation while inserted within the vertebrate subject. The device may be configured to administer the defined wavelength of electromagnetic radiation in combination with administration of a pharmaceutical composition. The defined wavelength of electromagnetic radiation may be configured to have a therapeutic effect on the vertebrate subject.

In some aspects, the method may further include administering a defined wavelength of electromagnetic radiation from the device while inserted within the vertebrate subject. The method may further include inserting the device comprising the biodegradable optical fiber within a blood vessel or lymph vessel of the vertebrate subject. The method may further include administering the defined wavelength of electromagnetic radiation to induce relaxation or dilation of a blood vessel wall or a lymph vessel wall. The method may further include administering the defined wavelength of 440 to 470 nanometers from the device while inserted within the vertebrate subject.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
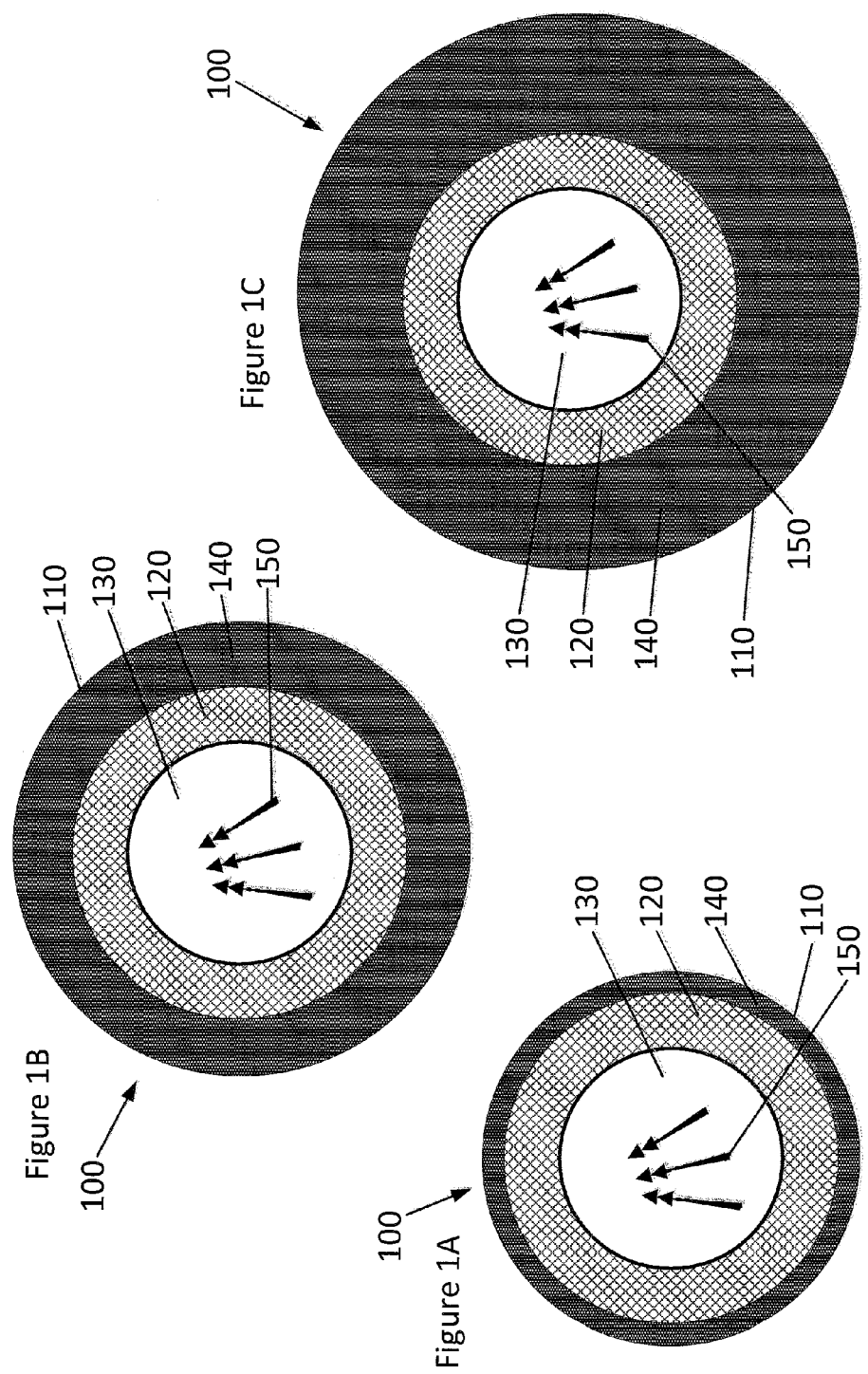
FIGS. 1A, 1B, and 1C depict a diagrammatic view of an aspect of a device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A device and methods of use thereof are disclosed herein for a biodegradable optical fiber and a method of producing a device including a biodegradable optical fiber for biomedical therapeutics, biomedical diagnostics, or surgery. A device is disclosed that includes: a biodegradable optical fiber including: a biodegradable optically functional inner fiber including an optically-transmitting cladding in contact with and surrounding an optically-transmitting core, wherein the inner fiber is biodegradable on a first time scale; and an outer layer in contact with and surrounding the optically-transmitting cladding, wherein the outer layer is biodegradable on a controllably-defined delayed time scale, and the controllably-defined delayed time scale is of greater duration than the first time scale.

A method of producing a device including a biodegradable optical fiber is disclosed that includes: contacting and surrounding an optically-transmitting core with an optically-transmitting cladding to form a biodegradable optically functional inner fiber, wherein the inner fiber is biodegradable on a first time scale; and contacting and surrounding the optically-transmitting cladding of the optically functional inner fiber with an outer layer, and the outer layer is biodegradable on a controllably-defined delayed time scale, wherein the controllably-defined delayed time scale is of greater duration than the first time scale. In some aspects, the outer layer may comprise a single material. The outer layer may be less optically transmissive than the cladding or the core. The outer layer may have an index of refraction greater than that of the cladding. The contacting and the surrounding the optically-transmitting cladding of the optically functional inner fiber with the outer layer may be performed at a later time than the formation of the inner fiber.

A device is disclosed that includes: a photodegradable optical fiber including: a photodegradable optically functional inner fiber including an optically-transmitting cladding in contact with and surrounding an optically-transmitting core, wherein the inner fiber is photodegradable to yield biodegradable products. In some aspects, an outer layer in contact with and surrounding the optically-transmitting cladding, wherein the outer layer is biodegradable on a controllably-defined delayed time scale to yield biodegradable products, and the controllably-defined delayed time scale is longer than a time scale of photodegradation of the inner fiber. The outer layer may comprise a single material. The outer layer may be less optically transmissive than the cladding or the core. The outer layer may have an index of refraction greater than an index of refraction of the cladding. In some aspects, an outer layer may be in contact with and surrounding the optically-transmitting cladding, wherein the outer layer is photodegradable. The photodegradable outer layer may be responsive to defined wavelengths of light. The outer layer may comprise a single material. The outer layer may be optically transmissive for the defined wavelengths of light.

A method of producing a device including a photodegradable optical fiber is disclosed that includes: contacting and surrounding an optically-transmitting core with an optically-transmitting cladding to form a photodegradable optically functional inner fiber. In some aspects, the method may include contacting and surrounding the optically-transmitting cladding of the photodegradable optically functional inner fiber with an outer layer, wherein the outer layer is photodegradable to yield biodegradable products. The outer layer may comprise a single material. The outer layer may be less optically transmissive than the cladding or the core. The outer layer may have an index of refraction greater than that of the cladding. In some aspects, the contacting and the surrounding the optically-transmitting cladding of the optically functional inner fiber with the outer layer may be performed at a later time than the formation of the inner fiber.

A method for diagnostic assay in a vertebrate subject is disclosed that includes: inserting within a vertebrate subject a device comprising a photodegradable optical fiber including: a photodegradable optically functional inner fiber including an optically-transmitting cladding in contact with and surrounding an optically-transmitting core, wherein the inner fiber is configured to photodegrade to yield biodegradable products; wherein the device is configure to determine a biological parameter while inserted within the vertebrate subject.

A method for treating a disease or condition in a vertebrate subject is disclosed that includes: inserting within a vertebrate subject a device comprising a photodegradable optical fiber including: a photodegradable optically functional inner fiber including an optically-transmitting cladding in contact with and surrounding an optically-transmitting core, wherein the inner fiber is configured to photodegrade to yield biodegradable products in response to a first defined wavelength of light; wherein the device is configured to administer a second defined wavelength of electromagnetic radiation while inserted within the vertebrate subject. The device may be configured to administer the second defined wavelength of electromagnetic radiation in combination with administration of a pharmaceutical composition.

A method for treating a disease or condition may utilize a photodegradable optical fiber. The photodegradable optical fiber device may administer the first defined wavelength of electromagnetic radiation, wherein the first defined wavelength is configured to photodegrade the photodegradable optical fiber to yield biodegradable products. The device may administer the second defined wavelength of electromagnetic radiation, wherein the second defined wavelength is configured to have a therapeutic effect on the vertebrate subject. Photodegradable optical fibers may be used as: 1) light-based sensors of chemicals and cells; 2) conduits for light transmission to organs, tissues and cells, (e.g., optogenetics), and 3) directed sources of irradiation to ablate tumor cells, bacteria and other targets. For functional use of the optic fiber, the second defined wavelength of electromagnetic radiation is configured to have a therapeutic effect on the vertebrate subject. EM transmissions, for example, between approximately 400 nm to 750 nm, may be used to empower sensors, deliver light for imaging, and other biomedical applications. The implanted photodegradable optical fiber may be degraded in situ at any time by irradiating the photodegradable optical fiber with the first defined wavelength of electromagnetic radiation to initiate photodegradation and bio-degradation of the optical fiber. Photodegradation of the optically-transmitting cladding surrounding an optically-transmitting core may be initiated by irradiation, for example, with 300 nm wavelength light.

For example, the photodegradable optical fiber may be implanted within a blood vessel of a vertebrate subject to deliver light of a defined EM wavelength (440 to 470 nm) to a defined segment of the vasculature to induce relaxation or dilation of the blood vessel wall within the segment of the vascular tree in the mammalian subject. See, e.g., Sikka, et al., *Proc. Natl. Acad. Sci. USA*, 111: 17977-17982, 2014. Photodegradable optical fiber for medical implantation inside key blood vessels in the vertebrate subject may provide non-chemical dilation of the key blood vessels on command. Upon completion of the therapeutic protocol, photodegradation of the photodegradable optical fiber may be initiated. Photodegradation of the optically-transmitting cladding surrounding an optically-transmitting core of the photodegradable optical fiber may be initiated by irradiation, e.g., with 300 nm wavelength light.

A method for treating a disease or condition in a vertebrate subject is disclosed that includes: inserting within a vertebrate subject a device comprising a biodegradable optical fiber including: a biodegradable optically functional inner fiber including an optically-transmitting cladding in contact with and surrounding an optically-transmitting core, wherein the inner fiber is configured to biodegrade on a first time scale; and an outer layer in contact with and surrounding the optically-transmitting cladding, wherein the outer layer is biodegradable on a controllably-defined delayed time scale, and the controllably-defined delayed time scale is of greater duration than the first time scale. In some aspects, the device may be configured to administer a defined wavelength of electromagnetic radiation while inserted within the vertebrate subject. The device may be configured to administer the defined wavelength of electromagnetic radiation in combination with administration of a pharmaceutical composition. The defined wavelength of electromagnetic radiation may be configured to have a therapeutic effect on the vertebrate subject.

FIGS. 1A, 1B and 1C depict a diagrammatic view of an aspect of a device. A cross-sectional view of a that includes a biodegradable optical fiber 110 including: a biodegradable optically functional inner fiber 120, 130 including an optically-transmitting cladding 120 in contact with and surrounding an optically-transmitting core 130; and a non-optically-transmitting outer layer 140 surrounding and in contact with the optically-transmitting cladding 120, wherein the non-optically-transmitting outer layer 140 is biodegradable on a controllably-defined delayed time scale. The controllably-defined delayed time scale of the outer layer is based on differences in thickness FIG. 1A, FIG. 1B, FIG. 1C of the non-optically-transmitting outer layer 140.

Figure 2:
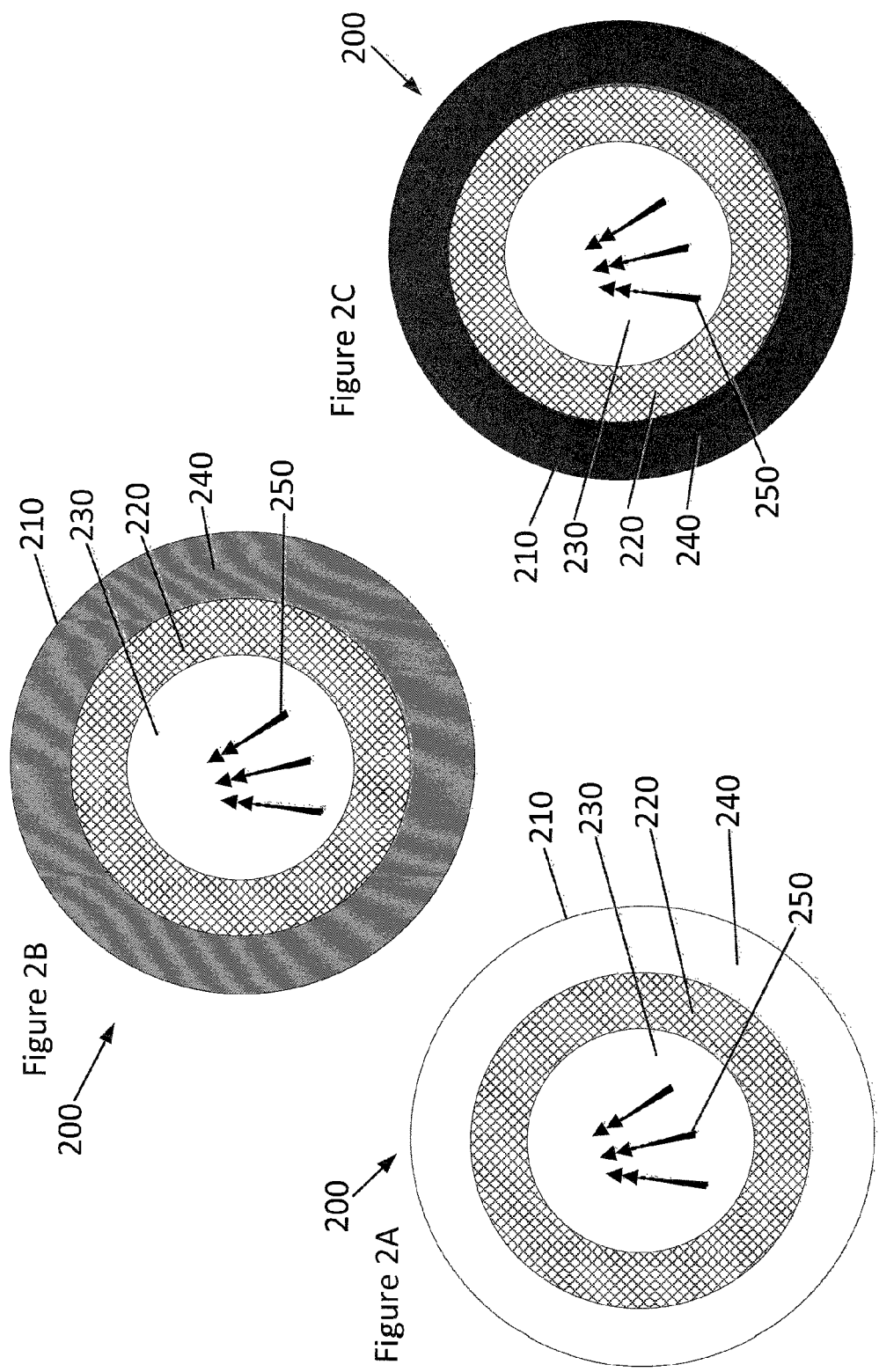
FIGS. 2A, 2B, and 2C depict a diagrammatic view of an aspect of a device.

FIGS. 2A, 2B, and 2C depict a diagrammatic view of an aspect of a device. A cross-sectional view of a device 200 that includes a biodegradable optical fiber 210 including: a biodegradable optically functional inner fiber 220, 230 including an optically-transmitting cladding 220 in contact with and surrounding an optically-transmitting core 230; and a non-optically-transmitting outer layer 240 surrounding and in contact with the optically-transmitting cladding 220, wherein the non-optically-transmitting outer layer 240 is biodegradable on a controllably-defined delayed time scale. The controllably-defined delayed time scale of the outer layer is based on based on differences in chemical composition FIG. 2A, FIG. 2B, FIG. 2C of the non-optically-transmitting outer layer 240.

For example, the non-optically-transmitting outer layer 240 may be composed of cellulose derivatives, e.g., esters and ethers. Cellulose fibers degrade rapidly in situ, while cellulose derivatives, e.g. esters and ethers, are more durable with lifespans in weeks and months. Biodegradation rates of cellulose esters depend on the degree of esterification. Specific adducts to cellulose, e.g., hydroxypropyl methyl cellulose, cellulose acetate, and cellulose butyrate differ in their biodegradation times. Other polymers may be used to coat the optic fibers and control their rate of biodegradation in vivo. For example, amylose, amylopectin, starch, lignins, pectins, chitin, chitosan, poly (lactide) and poly (glycolide) may be used to create coatings that are stable to degradation for days or up to years.

Figure 3:
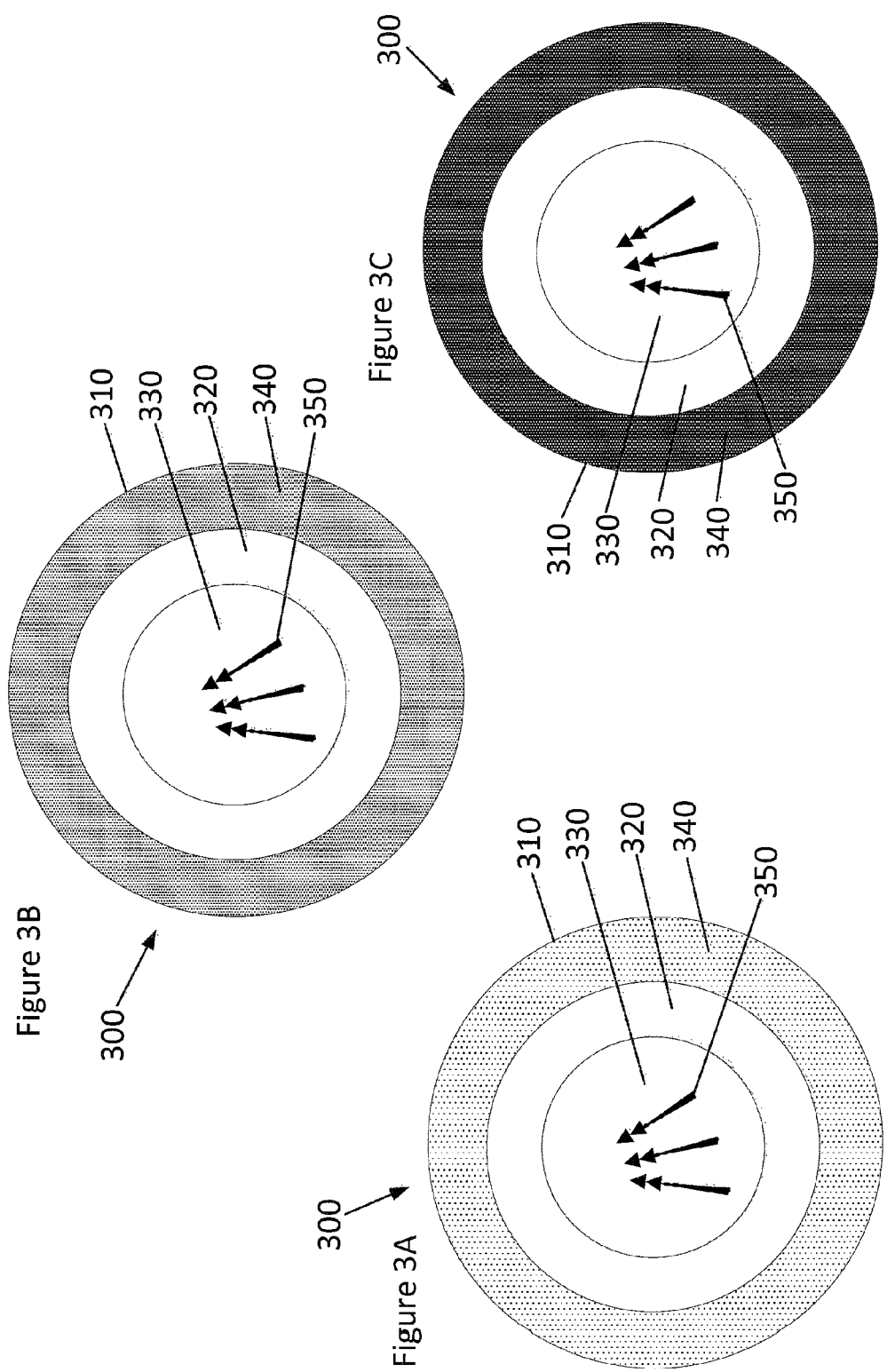
FIGS. 3A, 3B, and 3C depict a diagrammatic view of an aspect of a device.

FIGS. 3A, 3B, and 3C depict a diagrammatic view of an aspect of a device. A cross-sectional view of a device 300 that includes a biodegradable optical fiber 310 including: a biodegradable optically functional inner fiber 320, 330 including an optically-transmitting cladding 320 in contact with and surrounding an optically-transmitting core 330; and a non-optically-transmitting outer layer 340 surrounding and in contact with the optically-transmitting cladding 320, wherein the non-optically-transmitting outer layer 340 is biodegradable on a controllably-defined delayed time scale. The controllably-defined delayed time scale of the outer layer is based on based on differences in chemical composition FIG. 3A, FIG. 3B, FIG. 3C of the non-optically-transmitting outer layer 340.

For example, the non-optically-transmitting outer layer 340 may be composed of cellulose derivatives, e.g., esters and ethers, of varying density that affects its rate of degradation. As a further example, the non-optically-transmitting outer layer 340 may be a photodegradable polymer may have varying composition or density affecting its rate of degradation upon exposure to UV light.

Figure 4:
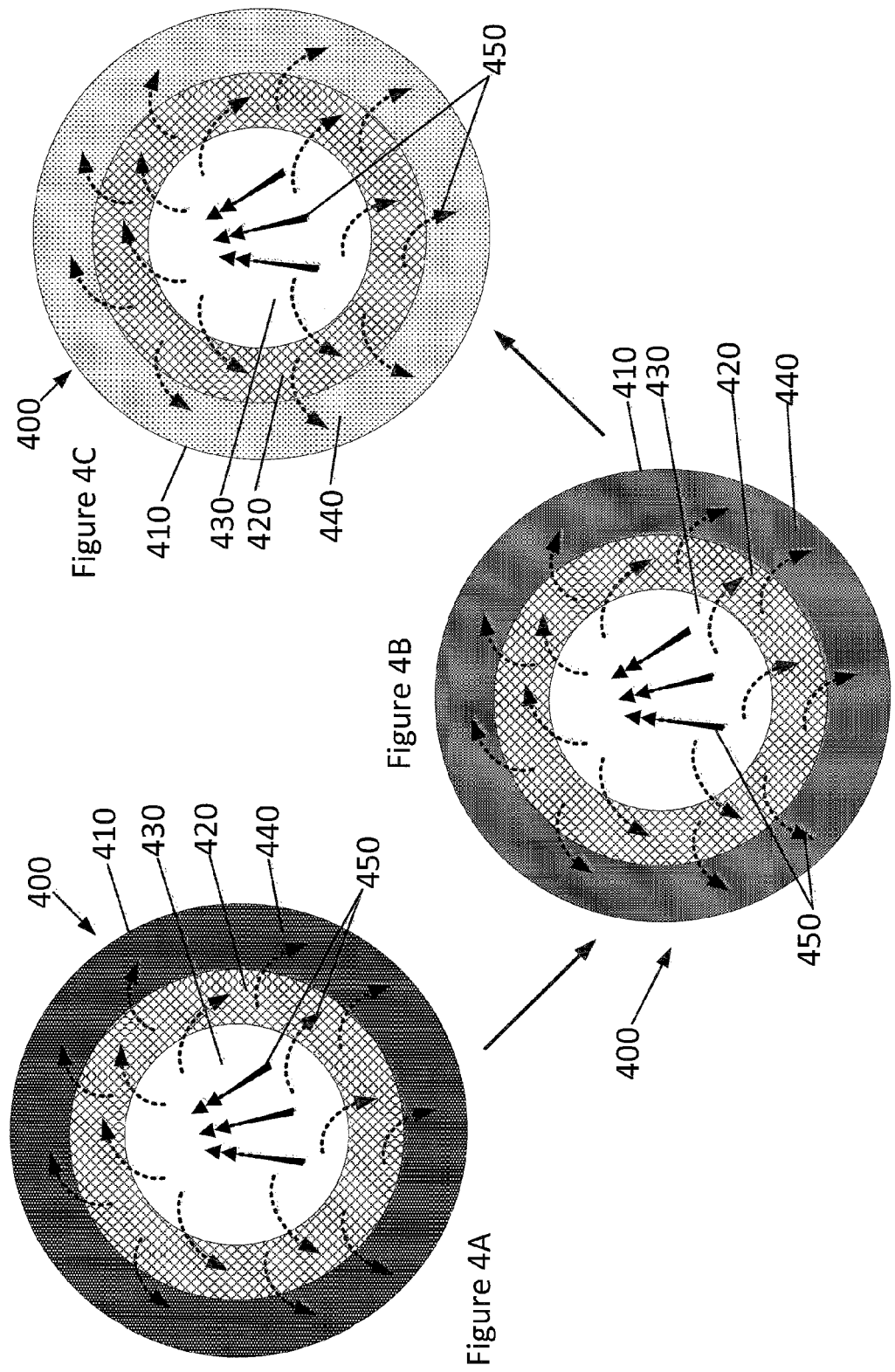
FIGS. 4A, 4B, and 4C depict a diagrammatic view of an aspect of a device.

FIGS. 4A, 4B, and 4C depict a diagrammatic view of an aspect of a device. A cross-sectional view of a device 400 that includes a biodegradable optical fiber 410 including: a biodegradable optically functional inner fiber 420, 430 including an optically-transmitting cladding 420 in contact with and surrounding an optically-transmitting core 430; and a non-optically-transmitting outer layer 440 surrounding and in contact with the optically-transmitting cladding 420, wherein the non-optically-transmitting outer layer 440 is biodegradable on a controllably-defined delayed time scale. The controllably-defined delayed time scale of the outer layer is based on electromagnetic radiation 450 from the optically-transmitting core 430 penetrating a lossy optically-transmitting cladding 420 to impinge upon a photodegradable composition [FIG. 4A→FIG. 4B→FIG. 4C] in the non-optically-transmitting outer layer 440 and progressively degrade the photodegradable composition.

A device 400 including a biodegradable optical fiber 410 is constructed with multiple biodegradable channels 420, 430 and a photodegradable external coating 440. An optical fiber with two concentric channels 420, 430 is constructed from polymers that biodegrade rapidly when exposed to physiological fluids. A concentric outer channel 420 is constructed with UV transparent polymers to leak UV light externally, i.e. radially, from the optic fiber 430. The outer channel 420 is a lossy UV fiber with a very thin cladding, which allows UV radiation (approximately 300 nm wavelength) to leak as evanescent waves that penetrate the cladding and escape from the fiber. A photodegradable coating 440 surrounds the outer cladding 420 and protects the optic fiber 420, 430 from biodegradation. Irradiation of the copolymer coating 440 with UV light results in cleavage of chemical bonds in the copolymer and degradation of the coating. The thickness and composition of the outer coating 440 may be modified to control the rate of photodegradation and the required UV irradiation.

Figure 5:
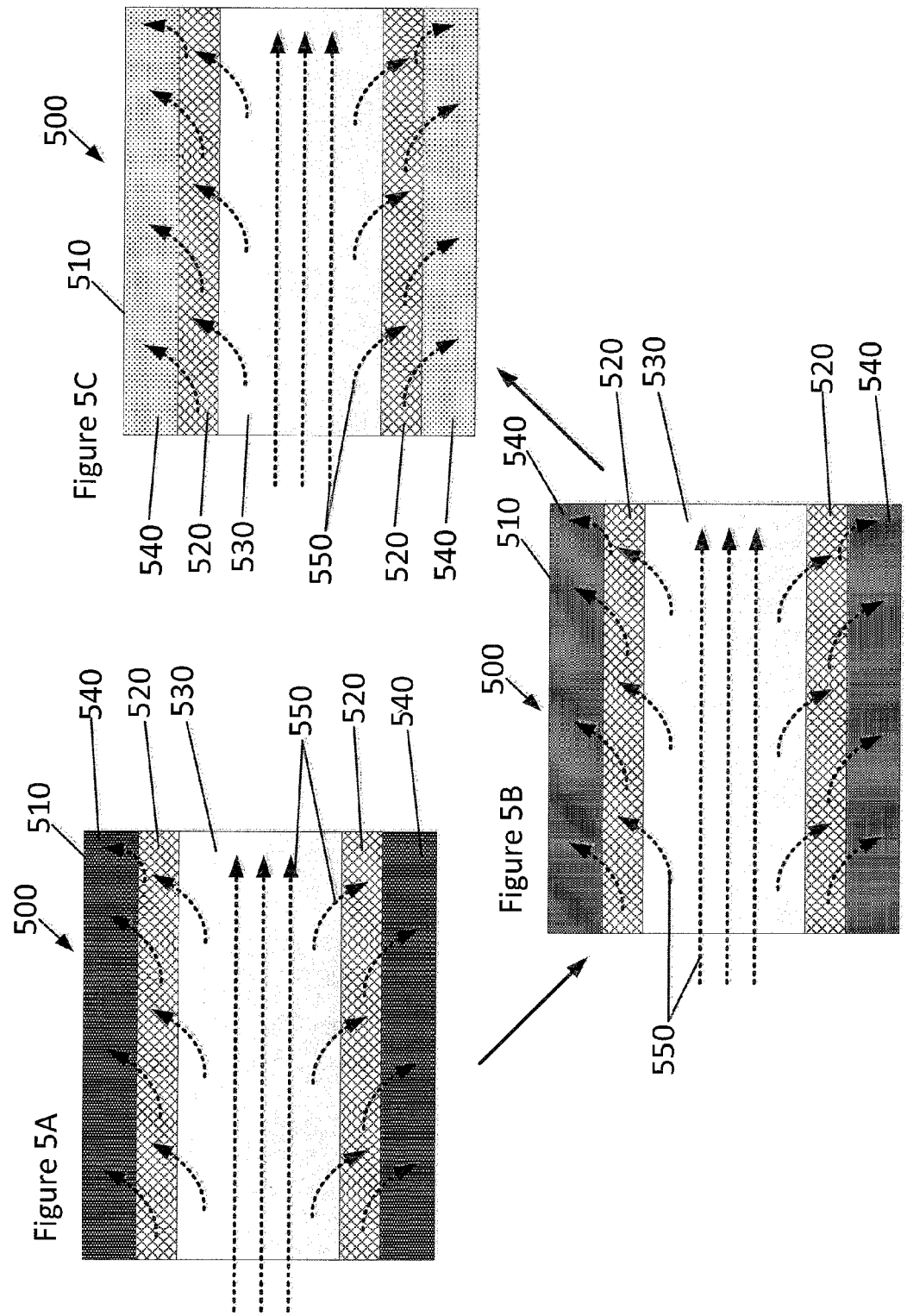
FIGS. 5A, 5B, and 5C depict a diagrammatic view of an aspect of a device.

FIGS. 5A, 5B, and 5C depict a diagrammatic view of an aspect of a device. A cross-sectional view of a device 500 that includes a biodegradable optical fiber 510 including: a biodegradable optically functional inner fiber 520, 530 including an optically-transmitting cladding 520 in contact with and surrounding an optically-transmitting core 530; and a non-optically-transmitting outer layer 540 surrounding and in contact with the optically-transmitting cladding 520, wherein the non-optically-transmitting outer layer 540 is biodegradable on a controllably-defined delayed time scale. The controllably-defined delayed time scale of the outer layer is based on electromagnetic radiation 550 from the optically-transmitting core 530 penetrating a lossy optically-transmitting cladding 520 to impinge upon a photodegradable composition [FIG. 5A→FIG. 5B→FIG. 5C] in the non-optically-transmitting outer layer 540 and progressively degrade the photodegradable composition.

Figure 6:
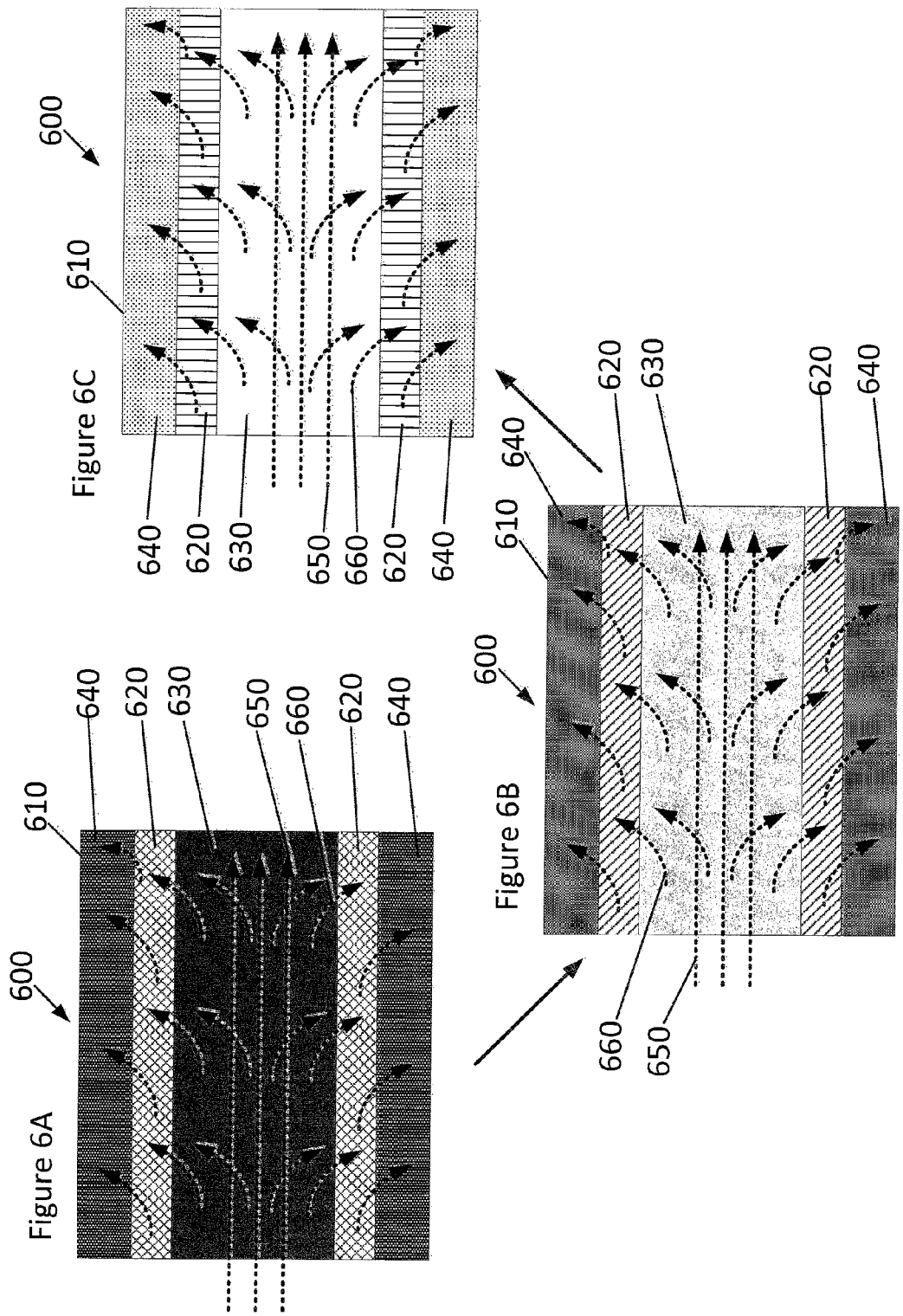
FIGS. 6A, 6B, and 6C depict a diagrammatic view of an aspect of a device.

FIGS. 6A, 6B, and 6C depict a diagrammatic view of an aspect of a device. A cross-sectional view of a device 600 that includes a photodegradable optical fiber 610 including: a photodegradable optically functional inner fiber 620, 630 including an optically-transmitting cladding 620 in contact with and surrounding an optically-transmitting core 630; and a non-optically-transmitting outer layer 640 surrounding and in contact with the optically-transmitting cladding 620, wherein the non-optically-transmitting outer layer 640 is photodegradable on a controllably-defined delayed time scale. The photodegradable optical fiber 610 permits passage of a first electromagnetic radiation 650 through the optically functional inner fiber 620, 630. The controllably-defined delayed time scale of the outer layer is based on second electromagnetic radiation 660 from the optically-transmitting core 630 penetrating a lossy optically-transmitting cladding 620 to impinge upon a photodegradable composition [FIG. 6A→FIG. 6B→FIG. 6C] in the non-optically-transmitting outer layer 640.

Figure 7:
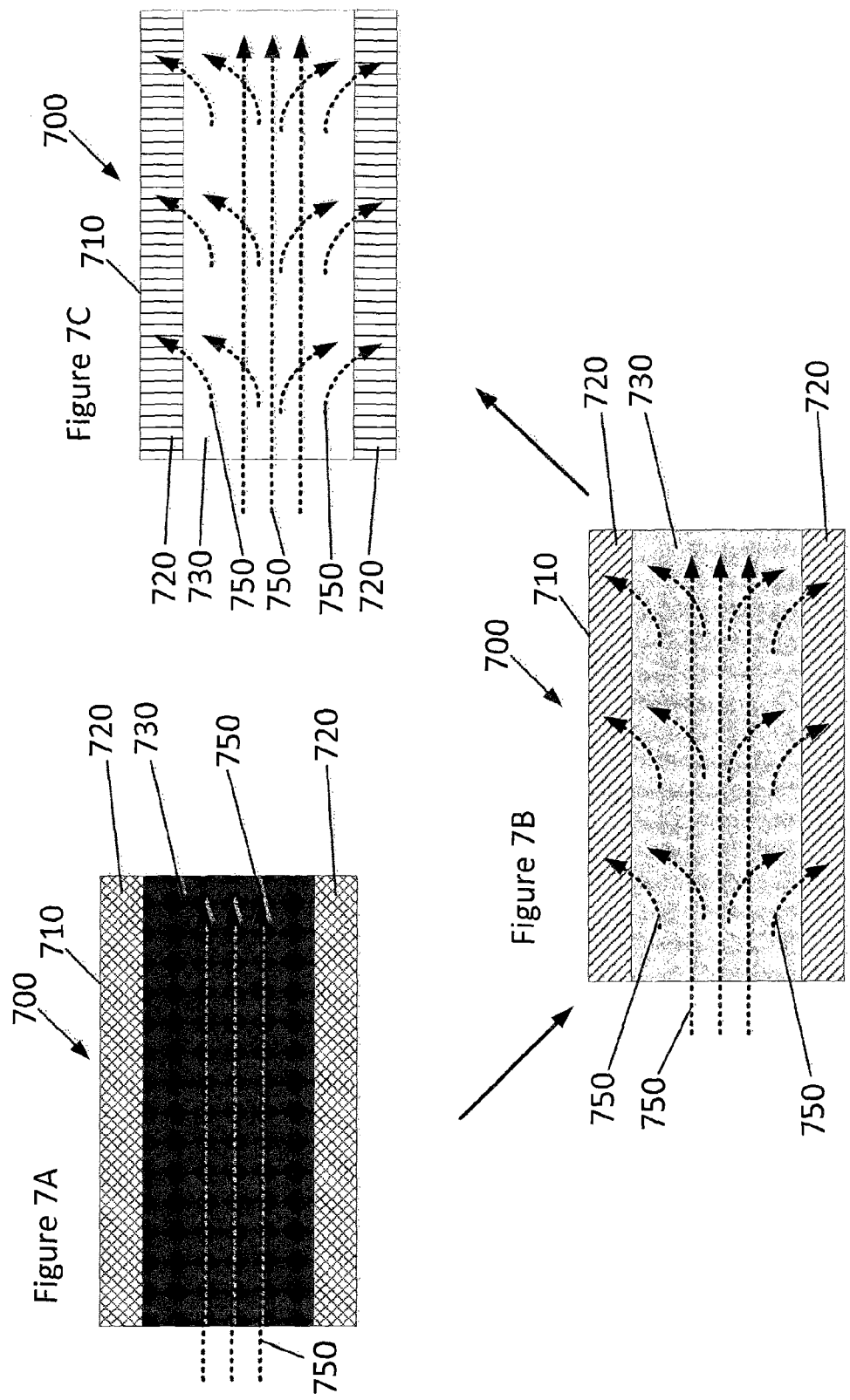
FIGS. 7A, 7B, and 7C depict a diagrammatic view of an aspect of a device.

FIGS. 7A, 7B, and 7C depict a diagrammatic view of an aspect of a device. A cross-sectional view of a device 700 that includes a photodegradable optical fiber 710 including: a photodegradable optically functional inner fiber 720, 730 including an optically-transmitting cladding 720 in contact with and surrounding an optically-transmitting core 730; wherein the photodegradable optical fiber 710 including the optically-transmitting cladding 720 in contact with and surrounding the optically-transmitting core 730 is photodegradable on a controllably-defined delayed time scale. The photodegradable optical fiber 710 permits passage of a first electromagnetic radiation 740, e.g., visible light, through the optically functional inner fiber 720, 730. The controllably-defined delayed time scale of the photodegradable optical fiber 710 is based on second electromagnetic radiation 750, e.g., ultraviolet light, transmitted through the photodegradable optical fiber 710, including the optically-transmitting core 730 and transmitted to penetrate the lossy optically-transmitting cladding 720 to impinge upon and degrade the photodegradable composition [FIG. 7A→FIG. 7B→FIG. 7C] in the photodegradable optical fiber 710.

Figure 8:
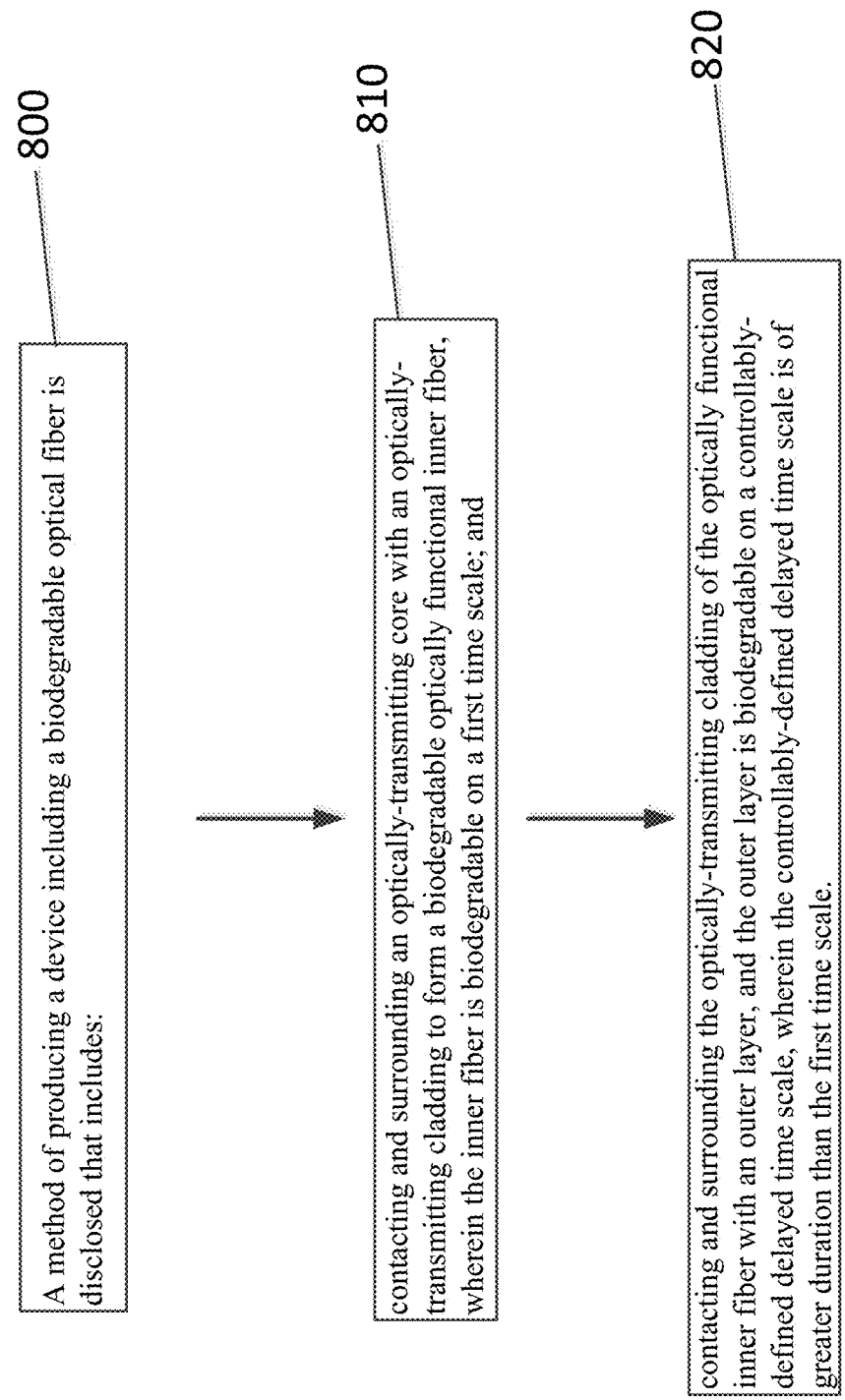
FIG. 8 depicts a diagrammatic view of an aspect of a method.

FIG. 8 depicts a diagrammatic view of an aspect of a method. A method of producing a device including a biodegradable optical fiber 800 comprising: contacting and surrounding 810 an optically-transmitting core with an optically-transmitting cladding to form a biodegradable optically functional inner fiber wherein the inner fiber is biodegradable on a first time scale; and contacting and surrounding 820 the optically-transmitting cladding of the optically functional inner fiber with an outer layer, and the outer layer is biodegradable on a controllably-defined delayed time scale, wherein the controllably-defined delayed time scale is of greater duration than the first time scale.

Figure 9:
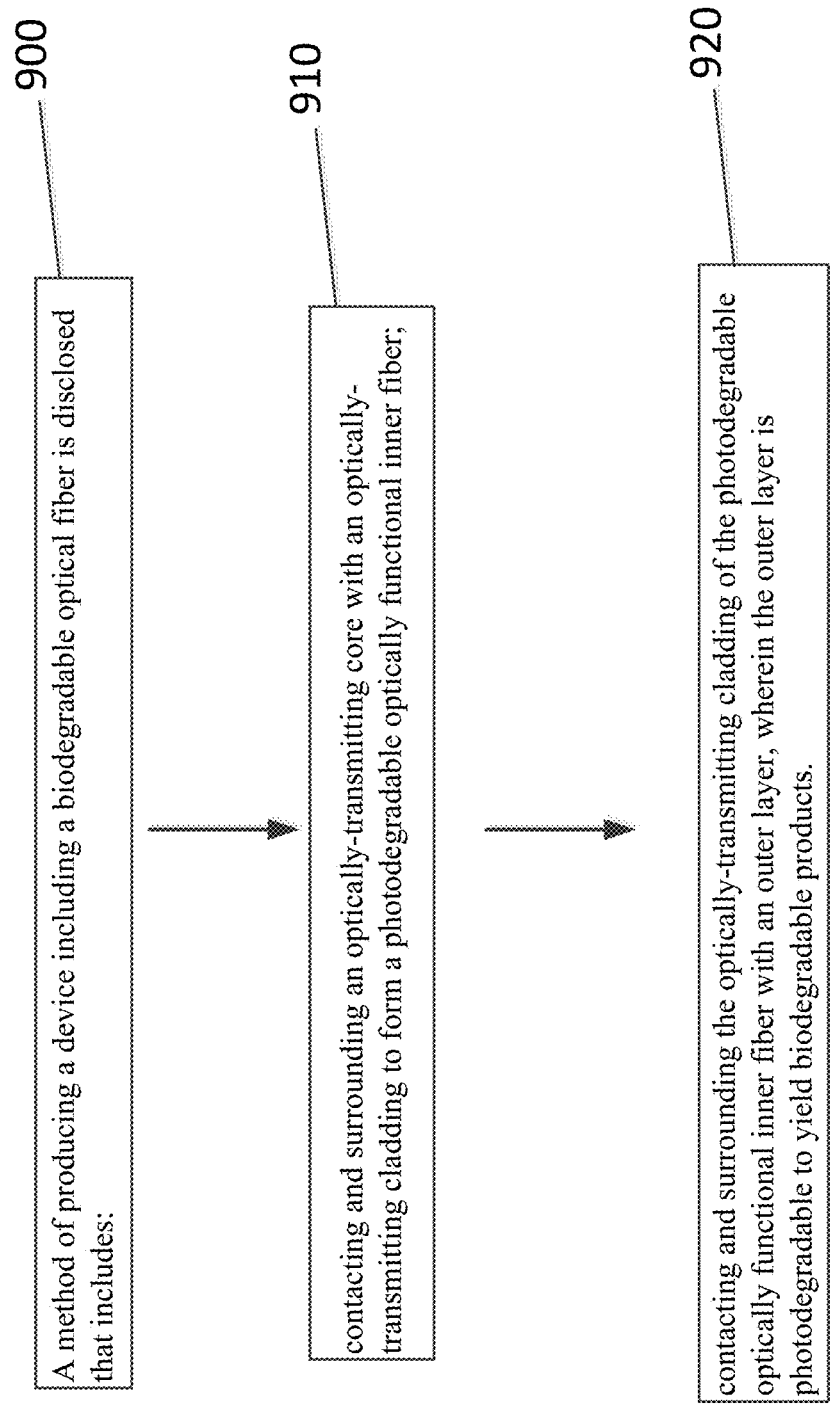
FIG. 9 depicts a diagrammatic view of an aspect of a method.

FIG. 9 depicts a diagrammatic view of an aspect of a method. A method of producing a device including a photodegradable optical fiber 900 comprising: contacting and surrounding 910 an optically-transmitting core with an optically-transmitting cladding to form a photodegradable optically functional inner fiber; and contacting and surrounding 920 the optically-transmitting cladding of the photodegradable optically functional inner fiber with an outer layer, wherein the outer layer is photodegradable to yield biodegradable products.

Biodegradable Optical Fibers for Targeted Dilation of Blood Vessel Wall within a Segment of the Vascular Tree in the Mammalian Subject A biodegradable optical fiber for medical implantation is manufactured with an outer coating formulated to undergo timed degradation in vivo. The outer coating is composed of biocompatible polymers selected to control the rate of degradation and the lifespan of the optical fiber according to its intended purpose. Alternatively, biodegradable optical fiber for medical implantation is manufactured with a photodegradable outer layer coating that degrades when irradiated with UV light. Photodegradation of the outer layer coating exposes the optic fiber to tissues and fluids that will biodegrade the optic fiber.

For example, optical fibers may serve as tissue-embedded sensors or in situ laser power sources that function for hours, days, weeks, months or years prior to biodegradation. Photodegradable optical fibers may be used as: 1) light-based sensors of chemicals and cells; 2) conduits for light transmission to organs, tissues and cells, (e.g., optogenetics), and 3) directed sources of irradiation to ablate tumor cells, bacteria and other targets. The implanted photodegradable optical fiber may be degraded in situ at any time by irradiating the photodegradable outer layer coating and initiating photo-degradation and bio-degradation of the optical fiber.

A biodegradable optical fiber for medical implantation may be utilized for delivering light of a defined wavelength into one or more tissues of the mammalian subject. The biodegradable optical fiber may be inserted or implanted into a blood vessel of the vasculature to deliver light of a defined wavelength within the vascular tree of a defined segment of the vasculature of the mammalian subject. For example, the biodegradable optical fiber implanted within the blood vessel may deliver light of a defined wavelength (440 to 470 nm) to a defined segment of the vasculature to induce relaxation or dilation of the blood vessel wall within the segment of the vascular tree in the mammalian subject. See, e.g., Sikka, et al., *Proc. Natl. Acad. Sci. USA*, 111: 17977-17982, 2014. Biodegradable optical fiber for medical implantation inside key blood vessels in the mammalian subject may provide non-chemical dilation of the key blood vessels on command.

Biodegradable Optical Fibers

Biodegradable optical fibers refer to components of an optical fiber that specifically degrade relative to presence or absence of a variety of conditions that include a variety of physiological conditions such as in vivo conditions of a vertebrate subject. The degradation products of biodegradable optical fibers are non-toxic and biocompatible with the physiology of the vertebrate subject.

Biodegradable optical fiber is constructed from polymers that undergo hydrolysis in vivo and are biocompatible. For example, cellulose butyrate and hydroxypropyl cellulose can be incorporated into an optical fiber preform (i.e., precursor) and drawn into optical fibers after heating the preform to approximately 180° C. Fibers with transparency windows (i.e., light transmission wavelengths) of 700 nm-1100 nm may be obtained. Biocompatible optical fibers may be manufactured from cellulose esters, e.g., cellulose butyrate and hydroxypropyl cellulose. See e.g., Dupuis et al., *Optics Letters* 32: 109-111, 2007, which is incorporated herein by reference. Optical fibers composed of cellulose derivatives may be rapidly hydrolyzed when exposed to tissues and fluids, especially in an acidic environment. Rapidly degrading optical fibers are coated with biocompatible polymers which degrade more slowly to control the lifespan of the fibers.

Optical fibers are composed of an inner core and an outer cladding that are rapidly degraded in vivo. The optical fibers may be coated in a biodegradable coating. The biodegradable coating degrades at a rate selected for the specific application. For example, an implanted optic fiber for sensing a biomarker of disease may be useful for 6 months or more to monitor an outpatient. Alternatively, a relatively short-lived optical fiber may be needed to monitor an internal wound and thus it may be coated with polymers known to degrade approximately 4 weeks after implantation, and an optic fiber for irradiation of tumor cells in situ may be coated with polymers that degrade after several weeks of tumor irradiation. Biocompatible polymer compositions may degrade in days, weeks, months or years. See e.g., Babak Ghanbarzadeh and Hadi Almasi (2013), *Biodegradable Polymers, Biodegradation—Life of Science*, Dr. Rolando Chamy (Ed.), ISBN: 978-953-51-1154-2, InTech, DOI: 10.5772/56230 which is incorporated herein by reference.

For example, cellulose fibers degrade rapidly in situ, while cellulose derivatives, e.g., esters and ethers, are more durable with lifespans in weeks and months. Biodegradation rates of cellulose esters depend on the degree of esterification. Specific adducts to cellulose, e.g., hydroxypropyl methyl cellulose, cellulose acetate, and cellulose butyrate differ in their biodegradation times. See e.g., Ghanbarzadeh and Almasi, Ibid. Other polymers may be used to coat the optic fibers and control their rate of biodegradation in vivo. For example, amylose, amylopectin, starch, lignins, pectins, chitin, chitosan, poly (lactide) and poly (glycolide) may be used to create coatings that are stable to degradation for days or up to years. For example, biodegradable polyesters tailored for controlled degradation may be synthesized from glycolide and lactide with degradation times ranging in weeks to months. See e.g., Biodegradable Polymers Info Sheet available online at: http://sigmaaldrich.com/technical-documents/articles/material-matters/resorner-biodegradeable-polymers.html which is incorporated herein by reference. Optical fiber coatings are applied during the drawing process. Degradable coatings of variable composition and different thickness may be incorporated into the optical fiber by surrounding the optical fiber during or after the drawing process. See e.g., U.S. Pat. No. 6,400,880 issued to Hebert et al. on Jun. 4, 2002 and U.S. Pat. No. 8,369,673 issued to Hawkes et al. on Feb. 5, 2013, which are incorporated herein by reference.

Optical Fibers Having Transparency Windows

A biodegradable optical fiber may include a biodegradable optically functional inner fiber including an optically-transmitting cladding in contact with and surrounding an optically-transmitting core. Optical fibers with transparency windows (i.e., light transmission wavelengths) may be obtained utilizing microstructured optical fiber composed of biodegradable and water soluble materials. Optical fibers with transparency windows of 700 nm-1100 nm may be obtained. Fabrication of a microstructured optical fiber may be composed of biodegradable and water soluble materials. The optical fiber may have a 1 dB/cm transmission loss. Two cellulose butyrate tubes separated with hydroxypropyl cellulose powder may be codrawn into a porous double-core fiber offering integration of optical, microfluidic, and potentially drug release functionalities.

The design and fabrication of a biodegradable polymer optical fiber may be used for optical, microfluidic, and drug release functionalities. The porous dual-core fiber structure presents a small inner core (which may be made hollow or filled) suspended in air by low refractive-index water-soluble particles separating it from the larger outer core. Geometry potentially permits multiple applications: the double-core structure allows efficient laser power delivery and improved collection of incoming light for passive sensing; the cladding porosity allows microfluidics, biosensing, and slow drug release by the water-soluble microstructure; a hollow core allows injection or slow release of therapeutic compositions. This geometry may be tailored to a given application by controlling the preform design and drawing processes.

The fiber preform may be prepared by using commercially available cellulose butyrate (CB) tubes (refractive index 1.475) of two different diameters. Values for the inner/outer diameters of the smaller and larger tubes are ⅛/¼ in., and ⅜/⅝ in., respectively. The smaller-diameter tube, which forms the inner of the two fiber cores, may be sealed at both ends with Teflon tape and placed in the middle of the larger tube that formed the outer core. In the final fiber structure the air hole of the inner tube may be collapsed or left open, depending on the application, by controlling fiber-drawing conditions. Space between the tubes may be then filled with a poly-disperse hydroxypropyl cellulose powder (refractive index of 1.337) to yield a lower-index inner cladding. The glass transition temperatures of cellulose butyrate and hydroxypropyl cellulose are 95° C. and 120° C., respectively. As the powder has a significantly higher melting temperature than the tubes, it remained in a powder state during the drawing process. The preform was preheated at a temperature of 150° C. for one hour, and the fiber was subsequently drawn at 180° C.

The biodegradable optical fiber may be drawn down to a diameter of 450 μm. A standard cutback measurement may be performed at λ=630 nm, resulting in a fiber transmission loss between 1 and 2 dB/cm, showing significant variation from one sample to another because of the random realization of the microstructure. Powder particles remain intact during the drawing process and may support the inner core and form a very porous inner cladding with an effective refractive index close to that of air. Ellipsometric measurements of the material losses of thick samples (<5 mm) of cellulose butyrate and polymethyl methacrylate (PMMA) are compared. At λ=630 nm, the cellulose butyrate material loss is 0.4 dB/cm, accounting for almost one half of the measured fiber loss. The cellulose butyrate transparency window (material loss <10 dB/m) is 700 nm≤λ≤1100 nm, for which several medical lasers exist. In this window several meters of cellulose butyrate fiber can be used, long enough for many medical applications. Overall, in the near-IR the cellulose butyrate and PMMA material losses are similar, while in the visible the PMMA transparency window is wider, 410 nm≤λ≤1100 nm.

Microstructured polymer optical fiber may be fabricated from two types of biodegradable cellulose to provide different glass transition temperatures. The resulting fiber has a porous double-cladding structure in which the inner core is suspended in the middle of an outer cladding by the intact powder particles. The inner core is a cellulose tube with a hole that may be collapsed, for laser delivery, or left open, for potential drug delivery. Transmission through the fiber first increases when it is filled with water, leveling off when fiber is filled completely and the microstructure is dissolved. The use of monodisperse particles with a choice of particle size may allow further tailoring the properties of such fibers for a variety of applications. See, e.g., Dupuis et al., *Optics Letters* 32: 109-111, 2007, which is incorporated herein by reference.

Manufacture of Optical Fibers

A device including a biodegradable optical fiber may be incorporated into a bandage. A biodegradable optical fiber as a bandage sensor may encompass any combination of a wound covering (e.g., a bandage) and a sensing component that is used to simultaneously cover and examine a wound or area of injury. Sensors may be associated with monitoring systems suitable for receiving and processing signals derived from the sensor. A pulse oximetry system may include a bandage sensor that includes a bandage with biodegradable waveguides and a pulse oximetry monitor. The biodegradable optical fiber as a bandage sensor may include an emitter for emitting light at one or more wavelengths via the biodegradable waveguides toward a patient's tissue. The emitter may be optically connected to the biodegradable waveguides via a fiber optic connector. A detector may also be provided in the bandage sensor for detecting the light passing through, reflected or fluoresced by the tissue of a patient through the biodegradable waveguides. The detector may be optically coupled to the biodegradable waveguides via a fiber optic connector.

As noted above, The biodegradable optical fiber as the bandage sensor may include biodegradable waveguides within a bandage structure, which may facilitate the medical examination of an injured area on a patient or may allow detection of an analyte for determination of a disease state. The material, shape and extent of the biodegradable waveguides may vary to suit the type or function of bandage sensor. The biodegradable waveguides may be formed from different materials that give rise to a number of different optical and physical properties. In addition, the biodegradable waveguides may have dimensions that allow the waveguides to function as single- or multimode optical guides, allowing a variety of light sources to be used as emitters, such as LEDs, broadband lamps, and lasers. The light sources may couple to the biodegradable waveguides via a conventional fiber optic cable or connector, a tapered lens or any similar feature. In some aspects, the biodegradable waveguides may be provided as a mesh that covers all or most of the patient contacting surface of the bandage sensor or may cover select portions of the bandage sensor (such as patterns, patches, strips, edges, and so forth) that provide sufficient area for analysis, as discussed herein.

In some aspects, the biodegradable waveguides may be multi-channel optical fibers, such as dual-channel optical fibers. Such fibers may be formed by drawing large diameter fibers and concentric, smaller diameter fibers into microfibers. For example, the diameter of the larger, outer fiber may be between about 1 mm and about 20 cm before drawing, and tens to hundreds of microns (μm) (e.g., about 10 μm to about 500 μm) afterwards. The smaller fibers (the inner fibers) may have initial diameters similar to that of the outer fiber (inasmuch as the inner fibers are able to be placed within the outer fiber). The drawing process may result in inner fibers with diameters in the range of 1 μm to 50 μm, resulting in single- or multi-mode optical fibers. The outer fiber may form an outer channel and outer cladding that is spaced from the smaller concentric fibers (that may form an inner channel and an inner cladding) by a support material that fills the outer channel. When the biodegradable waveguides are formed by such a drawing process, the biodegradable waveguides may exhibit properties resembling single- or multi-mode optical fibers, depending not only on the dimensions of the channels, but on which channel is coupled to the light source. That is, light propagating substantially down the multi-mode outer channel may have varying pathways. Light propagating substantially down the inner channel may or may not have varying pathways, depending on the size of the inner channel. The biodegradable waveguides may be implemented using multi-channel/multi-core biodegradable fibers or in dual-channel/dual-core fibers depending upon the needs of the application.

A dual-channel biodegradable fiber waveguide may be formed to include an outer cladding, an outer channel, an inner cladding and an inner channel for transmission of light to and from a tissue area of the patient. The outer and inner claddings may be formed from a biodegradable material, which may be any one or a combination of textiles. For example, textiles including poly (lactic acids), synthetic and natural silks, cellulose and its derivatives, chitin and chitosan derivatives, alignates, sugars, and poly (hydroxyalkanoates) may degrade away after a given amount of time after being disposed on or within a patient. In some aspects, the cladding material may be selected such that the material is transparent to wavelengths of interest, which may allow light to travel down the claddings as an evanescent wave. For example, in medical diagnostics, low-energy visible and near-IR wavelengths are often used. Thus, transparencies in the range 0.4 μm<λ<1.1 μm may be desirable (e.g., 0.7 μm≤λ≤1.1 μm). For example, materials such as hydroxypropyl cellulose, poly (methylmethacrylate) and cellulose butyrate may be used to construct the outer cladding and/or the inner cladding. In some aspects, the outer cladding and inner cladding may be formed from cellulose butyrate.

The outer channel may be formed, at least partially, using a material that is capable of supporting the inner cladding while enabling the outer channel to serve as a waveguide. Therefore, it may be desirable for the outer channel to be formed from a combination of materials that have refractive indices close to air, i.e., refractive indices close to 1. In related aspects, the materials may have a refractive index close to a medium, e.g., water, refractive index of about 1.33, that may fill the cores of the biodegradable fiber waveguide. In some aspects, it may be desirable that the light that propagates down the length of the outer channel does not experience significant loss (e.g., <10 dB/m) due to the support material and/or solution. Further, the outer channel may be formed from materials similar to those used in the inner cladding and outer cladding. The outer channel may include particles that support the inner cladding, for example, polydisperse hydroxypropyl cellulose powder (refractive index 1.337).

The size, shape, and extent of the particles may directly affect the waveguiding properties of the dual-channel fiber. In some aspects, it may be desirable for the support to be relatively stable during the processes used to form the dual channel fiber, for example, during the drawing process. In some aspects, the particles may have a glass transition temperature ($T_g$) higher than that of the fiber materials. The drawing process may be performed at a temperature higher than the $T_g$ of the fibers, such that the size and shape of the support particles is not substantially affected. In alternative aspects, it may be desirable to deform the size and shape of the support material, in which case materials may be chosen with $T_g$ similar to or lower than that of the fiber materials.

The inner channel may be formed from the drawing process. In some aspects, an inner fiber with an original (pre-drawing) diameter smaller than that of the original (pre-drawing) diameter of the outer fiber is drawn to a diameter such that the inner channel diameter approaches the dimensions of a single-mode optical fiber (e.g., between 1 μm and 50 μm, or between 8 μm and 10 μm). The exemplary dimensions may allow efficient delivery of light by medically useful laser modalities, such as Nd:YAG, Er:YAG, and $CO_2$, or LED and broadband lamp sources, such as tungsten-halogen lamps. See, e.g., U.S. Pat. No. 8,553,223, which is incorporated herein by reference.

Biodegradable Cellulose Polymers

Biodegradable optical fibers are composed of an inner core and an outer cladding that are rapidly degraded in vivo. The optical fibers may be coated in a biodegradable coating. The biodegradable coating degrades at a rate selected for the specific application. Biocompatible polymer compositions may degrade in days, weeks, months or years. For example, cellulose fibers degrade rapidly in situ, while cellulose derivatives, e.g. esters and ethers, are more durable with lifespans in weeks and months.

Cellulose is the main constituent of cell wall in lignocellulosic plant, and its content depends on the plant species, growing environment, position, growth, and maturity. Generally, cellulose content in lignocellulosic plant is 23-53% on a dry-weight basis, less than that in cotton, which is almost made of pure fibrous cellulose. In most straw species, approximately 35-45% of the dry substance is cellulose.

Chemical Structure of Cellulose

In the lignocellulosic materials, cellulose is embedded in a gel matrix composed of hemicelluloses, lignins, and other carbohydrate polymers. The combination of the chemical and the mechanical treatments is necessary for the dissolution of lignins, hemicelluloses, and other noncellulosic substances. A protocol based on acidified sodium chlorite is frequently applied to delignify woody materials as an initial step in the isolation of cellulose. Alkali extraction to dissolve hemicelluloses before or after delignification is the common method. The presence of high amounts of lignin in isolated cellulose fibers after delignification affects the structure and properties of the cellulose fibers. Fibers with high amounts of lignin are coarse and stiff, and have a brownish color. To obtain fibers that are relatively free of bound lignin, chemical bleaching may be utilized to obtain fibers with higher cellulose content from delignified and unbleached fibers. Chemical bleaching is usually considered as a continuation of delignification process to isolate cellulose from woody raw materials. Currently, there are various procedures for extraction of cellulose microfibrils, e.g., pulping methods, acid hydrolysis, steam explosion. Many useful properties stem from unique functional characteristics related to the chemical structure of cellulose. These structural properties include an extended, planar chain conformation and oriented, parallel-chain packing in the crystalline state. The absence of branches in this 100% linear polymer contributes to efficient chain packing in the native crystalline state, resulting in stiff, dimensionally stable fibers. Cellulose fibers thus exhibit a high degree of crystallinity (upwards of 70%) when isolated and purified. However, cellulose fibers present in native woody biomass exhibit approximately 35% crystallinity, due to the presence of other lignocellulosic components. The crystal nature (monoclinic sphenodic) of naturally occurring cellulose is known as cellulose I. Cellulose is resistant to strong alkali (17.5 wt %) but is easily hydrolyzed by acid to water-soluble sugars. Cellulose is relatively resistant to oxidizing agents. The tight fiber structure created by hydrogen bonds results in the typical material properties of cellulose, such as high tensile strength and insolubility in most solvents. There are significant differences between the properties of straw cellulose, wood cellulose, and cotton cellulose. The cellulose crystallites are longer in straw pulps than in wood pulps, but they are not as long as in cotton cellulose. In addition, the degree of crystallinity of straw pulps appears to be less than that of wood cellulose. Low crystallinity can be useful when a cellulose derivative is to be manufactured.

Optical fibers are composed of an optically-transmitting inner core and an optically-transmitting outer cladding that are rapidly degraded in vivo. The optical fibers may be coated in a biodegradable coating. The biodegradable coating degrades at a rate selected for the specific application. For example, an implanted optic fiber for sensing a biomarker of disease may be useful for 6 months or more to monitor an outpatient. Alternatively, a relatively short-lived optical fiber may be needed to monitor an internal wound and thus it may be coated with polymers known to degrade approximately 4 weeks after implantation, and an optic fiber for irradiation of tumor cells in situ may be coated with polymers that degrade after several weeks of tumor irradiation. Biocompatible polymer compositions may degrade in days, weeks, months or years.

For example, cellulose fibers degrade rapidly in situ, while cellulose derivatives, e.g. esters and ethers, are more durable with lifespans in weeks and months. Biodegradation rates of cellulose esters depend on the degree of esterification. Specific adducts to cellulose, e.g., hydroxypropyl methyl cellulose, cellulose acetate, and cellulose butyrate differ in their biodegradation times.

Optical fibers composed of an optically-transmitting inner core and an optically-transmitting outer cladding may be produced from chemically modified celluloses, principally cellulose esters. In all forms, cellulose is a very highly crystalline, high molecular weight polymer, which is infusible and insoluble in all but the most aggressive, hydrogen bond-breaking solvents, e.g., N-methylmorpholine-N-oxide. Because of its infusibility and insolubility, cellulose is usually converted into derivatives to make it more processable. All of the important derivatives of cellulose are reaction products of one or more of the three hydroxyl groups, which are present in each glucopyranoside repeating unit, including:

- ethers, e.g. methylcellulose, hydroxypropyl methyl cellulose and hydroxylethyl cellulose;
- esters, e.g. cellulose acetate, carboxymethyl cellulose and cellulose xanthate, which is used as a soluble intermediate for processing cellulose into either fiber or film forms, during which the cellulose is regenerated by controlled hydrolysis;
- acetals, especially the cyclic acetal formed between the C2 and C3 hydroxyl groups and butyraldehyde.

These modified forms of cellulose may be tailored to exhibit particular physical and chemical properties by varying the pattern and degrees of substitution within the cellulose backbone. Industrial applications are numerous and widespread for cellulose derivatives owing to rigidity, moisture vapor permeability, grease resistance, clarity, and appearance. Esterification of the cellulose backbone provides structural changes that allow for a greatly expanded range of applications, not available to the parent polysaccharide. Commercially available forms of cellulose acetate have degrees of substitution between 1.7 and 3.0 and are currently used in high volume applications for cellulose fiber production. Methylcellulose exhibits thermal gelation and has excellent film-forming properties. It has been widely used to prepare edible films. Carboxymethyl cellulose is also widely used in the pharmaceutical and food industries. It has good film forming properties. Carboxymethyl cellulose based film is a very efficient oxygen, carbon dioxide, and lipid barrier. However, it has poor resistance to water vapor transmission.

The chemically modified celluloses are degradable only under certain circumstances, as more recalcitrant, hydrophobic ester groups replace the native glucopyranosyl hydroxyls (to varying degrees) in the esterification procedure. Structurally, the degrees of substitution and C-2 hydroxyl substitution patterns are important criteria in predicting biodegradation patterns for these polymers. Biodegradation rates of cellulose esters generally increase with decreasing degrees of acetate substitution. See, e.g., Ghanbarzadeh and Almasi, 2013, *Biodegradable Polymers*, which is incorporated herein by reference.

Optical Fibers Having an Optically-Transmitting Cladding in Contact with and Surrounding an Optically-Transmitting Core Optical fiber coatings may be applied during the drawing process and degradable coatings of variable composition and different thickness are incorporated by surrounding the optical fiber. In some aspects, the optical fiber may include a biodegradable optically functional inner fiber including an optically-transmitting cladding in contact with and surrounding an optically-transmitting core. The biodegradable optically functional inner fiber includes an optically-transmitting core in contact with an optically-transmitting cladding that is a plastic coating. An opaque layer may also be formed on the plastic coating. The core may be about 2 μm to about 400 μm in diameter. In some aspects, the core may be about 10 μm in diameter. The core may be made of an optically transparent material such as glass. However, in some aspects, the core may be made of other materials, such as fluoroziconate, fluoroaluminate and chalcogenide glasses as well as crystalline materials like sapphire. Silica and fluoride glasses usually have refractive indices of about 1.5, but some materials such as the chalcogenides can have indices as high as 3. In some aspects, the core may be made of plastic optical fibers (POF) that may have a core diameter of 0.5 millimeters or larger.

The core may be surrounded by an optically-transmitting cladding that is a plastic coating having an outer diameter of about 5 μm to about 400 μm. In some aspects the diameter can be about 125 μm. In other aspects, the coating may have a diameter of about 50-500 μm. The covering of optical fiber core may be an external soluble coating or a biodegradable plastic coating. The outer plastic coating of raw optical fiber core may be substituted with a water-soluble plastic, e.g., a plastic containing corn starch. The plastic containing corn starch will degrade in a defined time period at a defined temperature while embedded within the body of the subject.

Another optically-transmitting cladding that is an optical fiber coating material is polyactic acid (PLA). PLA can be processed like most thermoplastics. Several forms of PLA exist including: poly-L-lactide (PLLA) and poly-D-lactide (PDLA) which form a highly regular stereocomplex with increased crystallinity. Biodegradation of PDLA and PLLA are slower than PLA due to the higher crystallinity.

The optically-transmitting cladding that is an optical fiber coating may be transparent or opaque. In some cases, light that is transmitted through the core may also be emitted through a transparent optical fiber coating. This illumination may be in the infrared optical region. The optical fiber coating may be opaque. An additive may be included to make the coating opaque. In some aspects, an additional opaque layer may be applied over the coating to prevent all light from being emitted by the optical fiber coating. The opaque layer may also be biodegradable and can dissolve in water like the coating.

While the biodegradable optical fiber is embedded within the body of the subject, the optically-transmitting cladding in contact with and surrounding an optically-transmitting core, and in some aspects the opaque layer, dissolve in the tissue of the subject. Eventually only the core material is left. The optically-transmitting core may be, for example, a co-axial glass core. Since the core is typically only 0.003 inch diameter, it will be extremely fragile without the protective covering. Any bending or physical contact may cause the optical core to mechanically break down in the body. Thus, the disposed fiber composed of its plastic coating and glass core, is quickly degradable and eliminated from the body. See, e.g., U.S. Pat. No. 8,369,673, which is incorporated herein by reference.

Optical Fibers Having a Non-Optically-Transmitting Outer Layer Composed of a Biodegradable Polymer/Calixarene Coating The non-optically-transmitting outer layer of the biodegradable optical fiber may be applied during the drawing process of the biodegradable optically-transmitting cladding in contact with and surrounding an optically-transmitting core. The non-optically-transmitting outer layer may be of variable composition and different thickness and is incorporated by surrounding the optical fiber. An optical fiber may include a core, a sheath, and a coating of non-opticallytransmitting outer layer made of polymer and calixarene. Calixarene binds to and stabilizes a compound of interest and is capable of releasing the compound of interest under defined conditions of temperature, and/or humidity and/or irradiation. Degradation of the non-optically-transmitting outer layer including the polymer and calixarene occurs under the defined conditions.

Calixarene in combination with a polymer is included in the non-optically-transmitting outer layer of the optical fiber. Calixarenes are compounds of the oligomeric cyclic phenol type used mainly in super-molecular chemistry and in which the successive phenol rings are linked through a —$CH_2$— group in the ortho position (positions 2, 5). These compounds have excellent compatibility with all types of polymers, in particular organic polymers, such as the polymers used for the non-optically-transmitting outer layer of the optical fiber.

Calixarenes do not react with the polymers, particularly organic polymers, under their general conditions of use. Therefore, no degradation of the polymer and fiber occurs by action of the calixarene, particularly under the conditions of storage. The presence of phenol rings in the structure of the calixarenes contributes to a very high thermal stability. The calixarenes in the non-optically-transmitting outer layer of the optical fiber include one or more known calixarenes, comprising 4 to 10 phenol rings, preferably 4, 5, 6 or 8 phenol rings, that is to say calix[4]arene, calix[5]arene, calix[6]arene or calix[8]arene. These calixarenes may possibly be substituted by one or more substituent groups chosen, for example, from among the linear or branched alkyl groups, alkenyl, aryl and aralkyl groups.

The chemical structure of the calixarene includes one or more phenol rings substituted in the para position by linear or branched alkyl groups with from 1 to 6 carbon atoms. In some aspects, the alkyl group is a tert-butyl group. For example, calixarene may be the t-butyl calixarene. Calixarenes may be generally represented by a basket or a cage capable of binding and trapping a molecule. The dimensions of this basket may be modulated according to the number of phenol molecules making it up and may therefore be matched to the size of the molecule of the compound to be liberated or a substrate.

Calixarene may act as the receptor. The receptor molecules are linked to one another by covalent bonds which are very strong and difficult to break. In contrast to this, the substrate is linked to the receptor. The cage formed by calixarene in which the substrate is bound by secondary bonds of the $\pi$-$\pi$ type are much easier to break and finally enables the substrate to be released. The substrate is a compound capable of being released under defined conditions of temperature and/or humidity and/or irradiation to bring about degradation of the non-optically-transmitting outer layer.

Each molecule of calixarene may bind to a single molecule or chemical entity or several molecules or chemical entities of the compound or compounds. Depending on the dimensions of the calixarene, for example, 2, 3, 4, 5 or 6 molecules or chemical entities which may be identical or different, may be bound inside the calixarene. Calixarenes may release the bound molecule or molecules under defined conditions of humidity and/or temperature and/or irradiation. The bound molecules or chemical entities are released only occurs under well-defined conditions, and only when the optical fiber and, in particular, the non-optically-transmitting outer layer are exposed to these specific conditions. See, e.g., U.S. Pat. No. 6,400,880, which is incorporated herein by reference.

Lossy Optical Fibers in a Optically-Transmitting Cladding of a Biodegradable Optical Fiber that Allow Light Leakage There are several possible ways to modify the fiber optics of a biodegradable optical fiber to allow light to leak out the sides of the biodegradable optically functional inner fiber as it propagates through the optical fiber. A concentric outer channel is constructed with UV transparent polymers to leak UV light externally, i.e. radially, from the optic fiber. The optically-transmitting cladding of the optical fiber may be a lossy UV fiber with a very thin cladding, e.g., approximately 1 micron thick, that allows UV radiation (approximately 300 nm wavelength) to leak as evanescent waves that penetrate the optically-transmitting cladding and escape from the optically-transmitting core of the optical fiber.

An optical fiber traps light propagating nearly along its axis by the phenomenon of total internal reflection that occurs when an incident light ray grazes a surface of a medium, e.g., a optically-transmitting core, in contact with a medium, e.g., an optically-transmitting cladding, of lower index of refraction. In general, the light must be coupled into the fiber in such a manner that all the optical rays are confined to angles of incidence less than the minimum for total internal reflection. When a reflected light ray reflects from the surface, an "evanescent wave" propagates into the low index medium, e.g., the optically-transmitting cladding layer, for a depth of a few wavelengths. For example, an incident ray will have an angle of incidence greater than the maximum for total internal reflection to occur. The light escapes from the optically-transmitting core as a transmitted ray.

Most optically-transmitting cladding layers are many wavelengths thick. In some aspects, a region of thin optically-transmitting cladding is only a few wavelengths thick. In this case, the evanescent wave can emerge to propagate as a real, transmitted ray outside the fiber. The reflected light ray will have less energy than incident light ray. Therefore, if the optically-transmitting cladding can be made thin enough a portion of the light will be lost from the optical fiber. When one considers UV radiation in the range of 300 nm wavelength, this implies that an optical fiber would have to be manufactured with an optically-transmitting cladding thickness of about 1 micron, which is achievable. Such an optical fiber would leak light by evanescent wave propagation along its entire length.

There are several ways to produce a lossy fiber including an optically-transmitting cladding. In some aspects, there are intermittent light "holes" spaced along the fiber which allow UV to escape from the fiber. In some aspects, there are 100 micron sized divots spaced in the cladding. Such light "holes" may be made by, for instance, but not limited to, an etching or machining operation conducted in a dry environment. A UV transparent cladding patch may be added immediately afterwards.

In a further aspect, loss from the optical fibers may be induced by creating a bend in the fibers. Curvature in the fiber allows incident light rays striking the concave surface to be at a higher angle of incidence, thereby allowing them to leak out as transmitted light rays. Smaller radii of curvature generate larger leak rates.

In some aspects, lossy fiber mats of optically-transmitting cladding are produced by optical fibers being woven around stiff fibers running normal to the optical fibers. This produces regular bending in the fibers in alternating directions resulting in a uniform light leakage rate.

In further aspects, although lossy fiber mats are produced by interweaving the lossy optical fibers with structural fibers, the light loss from the fiber may be, in part, by mechanisms other than the bending of the optical fibers, for example by mechanisms including, but not limited to, evanescent wave transmission through thin cladding.

Reflective mirrors may be added at the end of the optical fibers to get more uniform distribution of light loss. A single light-transmitting, leaky fiber may run back and forth to make the light loss more uniform. This light-transmitting, leaky fiber may be interwoven either with other light-transmitting, leaky fiber or with other structural fibers. Because there more light may be emitted from the light-transmitting, leaky fiber nearer to the source of illumination and less light at the far end, by doubling up the fiber by running it back and forth or putting a mirror on it would make the light loss to be more equal along the length. Multiple light sources may be used, i.e., light is feed into both ends of the fiber. The light-transmitting, leaky optical fiber may be illuminated by side launch. Just as light can exit a bent fiber, light can enter it. By wrapping the optical fibers around a light source enough light may be feed into the fiber to affect curing. The lossy optical fiber or the optically-transmitting cladding may be incorporated into either a supported or an unsupported film adhesive. The supported film adhesive may be designed with woven or unwoven scrims. See, e.g., U.S. Pat. No. 6,835,679, which is incorporated herein by reference.

Biodegradable Optical Fiber Including a Non-Optically-Transmitting Outer Layer that is a Photodegradable Coating The biodegradable optical fiber may include a photodegradable coating as a non-optically-transmitting outer layer that surrounds the biodegradable optically functional inner fiber and protects the optic fiber from biodegradation. A variety of photodegradable materials may be used for the non-optically-transmitting outer layer of the biodegradable optical fiber. For example, the photodegradable layer may be a blend of polymers, which includes a base or synthetic polymer and small amount of UV photodegradable keto carbonyl containing polymer. The amount of keto carbonyl groups in the composition may range from about 0.01 wt % to about 5 wt %, based upon the total weight of the base polymer. The keto carbonyl group is a ketone functional group characterized by a carbonyl group (O=C) linked to two other carbon atoms. The keto carbonyl group may be generally designated as $R_1(CO)R_2$.

The base or synthetic polymer may comprise a vinylidene monomer which is compatible with the keto carbonyl groups. "Compatible" may refer to polymers which can be blended together in the desired proportions to give a polymer blend of reasonable strength and toughness. The vinylidene monomer may comprise ethylene, styrene, methyl acrylate, methyl methacrylate, vinyl acetate, methacrylonitrile, acrylonitrile, vinyl chloride, acrylic acid, methacrylic acid, chlorostyrene, alpha-methylstyrene, vinyl toluene or butadiene. For example, a blend of polyethylene and about 9.5 wt % methylenemethyl isopropenyl ketone copolymer may be utilized. The polyethylene may be low density or high density. As a further example, a copolymer of 95 wt % styrene and 5 wt % methylisopenylketone may be utilized.

The non-optically-transmitting outer layer includes a polymeric composition that may also include a condensation copolymer and at least one ketone copolymer in which the amount of the ketone copolymer ranges from about 0.01 wt % to about 5 wt %. The condensation copolymer may comprise one or more of polyamides, polyesters, polyurethanes, polyethers, polyepoxides, polyamide esters, polyimides, poly(amide-imides), polyureas, and polyamino-acids.

An additional copolymer of a similar vinylidene monomer and an unsaturated ketone may be added in minor proportion. A minor proportion of a UV photodegradable copolymer may be utilized based upon one of the monomers of a synthetic polymer. For example, compositions may include blends of polystyrene (major proportion) and keto-carbonyl containing copolymers of styrene (minor proportion), blends of polymethylmethacrylate (major proportion) and keto-carbonyl containing copolymers of methyl-methacrylate (minor proportion), blends of polymethylacrylate (major proportion) and keto-carbonyl containing copolymers of methylacrylate (minor proportion), and blends of polyethylene (major proportion) and keto carbonyl containing ethylene-unsaturated ketone copolymers (minor proportion), being macro-molecular. The amount of keto carbonyl groups in the composition may range from about 0.01 wt % to about 5 wt %.

The keto copolymers may be utilized in minor proportion in the compositions and are themselves photodegradable on exposure to UV radiation. The keto copolymers may contain from about 0.01-10 wt %, or from about 0.01-5 wt %, or from about 0.02-2 wt % of a ketone carbonyl group. They are compatible with the base polymer (i.e., the synthetic polymer) with which they are to be blended. In the case of addition keto copolymers, the keto groups are located in a side chain at a position immediately adjacent to the backbone polymeric chain. In the case of condensation keto copolymers, the keto groups may be located either in a side chain as mentioned above, or in the polymer backbone. The keto copolymer may be blended with the synthetic polymer so as to give a polymeric composition preferably containing not more than 3 wt % keto groups in these preferred compositions. See e.g., US 2010/0249912, which is incorporated herein by reference.

Optical Fibers in Medical Diagnostic Devices

A medical diagnostic device including a biodegradable optical fiber may be used to measure various biological parameters, e.g., near infrared spectroscopy or pulse oximetry, in a patient. Near infrared spectroscopy (NIRS) is a noninvasive, portable technology similar to pulse oximetry, which monitors oxygenation in the brain, muscle, and other organs to detect tissue hypoxia-ischemia in real-time. NIRS uses near-infrared light (700 to 900 nm) and hardware similar to pulse oximetry to monitor the tissue bed beneath the sensor containing a mixed vascular oxygen saturation dominated by small gas-exchanging vessels (arterioles, capillaries, and venules). Two commercially available NIRS devices are INOVS (Covidien Corporation [formerly Somanetics], Troy, Mich.) and FORESIGHT (CAS Medical Systems [CASMED], Branford, Conn.), that are cleared by the Food and Drug Administration (FDA) for use in pediatrics and adults. These two devices differ with respect to design, hardware, and algorithm to determine regional cerebral oxygen saturation ($rScO_2$), and possess limitations. The Covidien device was cleared to monitor changes in $rScO_2$ in infants and children, whereas the CASMED device measures absolute $rScO_2$ but was validated in a narrow patient population. Nonin Medical, Inc (Plymouth, Minn.) has developed a NIRS device (EQUANOX) cleared by the FDA for use in adults and children greater than 40 kg. This device utilizes a dual-emitter/dual-detector sensor and dynamic compensatory algorithms which more effectively eliminate skin and bone contamination to focus on the underlying tissue. The device automatically adjusts for variations in tissue optical properties to improve accuracy over a wide range of age and physiologic condition.

The Nonin NIRS EQUANOX device may be calibrated (phase I) and validated (phase II) with a new small sensor to measure $rScO_2$ in children less than 40 kg with cardiovascular disease undergoing cardiac catheterization. See, e.g., Kreeger et al., *Ann. Thoracic Surg.* 94: 1527-33, 2012, which is incorporated herein by reference.

A Device Including a Biodegradable Optical Fiber as Fiber-Optic Biomedical Sensors A medical diagnostic device including a biodegradable optical fiber in a biomedical sensor may be used to measure various biological parameters. Optical fiber sensors comprise a light source, optical fiber, external transducer, and photodetector. Optical fiber sensors sense by detecting the modulation of one or more of the properties of light that is guided inside the fiber, e.g., intensity, wavelength, or polarization. The modulation is produced in a direct and repeatable fashion by an external perturbation caused by the physical parameter to be measured. The measurand of interest is inferred from changes detected in a property of the light.

Fiber-optic sensors that include a biodegradable optical fiber may be intrinsic or extrinsic. In an intrinsic sensor, the light never leaves the fiber and the parameter of interest affects a property of the light propagating through the fiber by acting directly on the fiber itself. In an extrinsic sensor, the perturbation acts on a transducer, and the optical fiber simply transmits light to and from the sensing location.

Fiber-optic sensing mechanisms have been demonstrated for biomedical applications and for industrial applications. Fiber-optic sensing mechanisms include, but are not limited to, fiber Bragg gratings (FBG), Fabry-Perot cavities or external fiber Fabry-Perot interferometer (EFPI) sensors, evanescent wave, Sagnace interferometer, Mach-Zehnder interferometer, microbend, photoelastic. The most common are based on EFPIs and FBGs. Spectroscopic sensors based on light absorption and fluorescence may also be used.

Biomedical fiber-optic sensing may be categorized into four main types: physical, imaging, chemical, and biological. Physical sensors measure a variety of physiological parameters, such as body temperature, blood pressure, and muscle displacement. Imaging sensors encompass both endoscopic devices for internal observation and imaging, as well as more advanced techniques such as optical coherence tomography (OCT) and photoacoustic imaging where internal scans and visualization can be made nonintrusively. Chemical sensors rely on fluorescence, spectroscopic, and indicator techniques to identify and measure the presence of particular chemical compounds and metabolic variables, such as pH, blood oxygen, or glucose level. Chemical sensors detect specific chemical species for diagnostic purposes, as well as monitor the body's chemical reactions and activity. Biological sensors rely on biological recognition reactions, such as enzyme-substrate, antigen-antibody, or ligand-receptor, to identify and quantify specific biochemical molecules of interest.

TABLE 1

Classification of biomedical sensors by type showing various biomedical parameters of interest

| Physical | Chemical | Biological | Imaging |
|---|---|---|---|
| Body temperature | pH | Antigen | Endoscopy |
| Blood pressure | $pO_2$ | Antibody | Optical coherence tomography (OCT) |
| Blood flow | $pCO_2$ | Electrolytes | Photodynamic therapy (PDT) |
| Heart rate | Oximetry ($SaO_2$, $SvO_2$) | Enzyme | |
| Force | Glucose | Inhibitors | |
| Position | Bile | Metabolites | |
| Respiration | Lipids | Proteins | |
| Shape sensing | | | |

See, e.g., "Medical Applications of Fiber Optics"; *LaserFocusWorld*, which is incorporated herein by reference.

PROPHETIC EXEMPLARY EMBODIMENTS

Prophetic Example 1: A Biodegradable Optical Fiber for Tissue Implantation

A biodegradable optical fiber for medical implantation is manufactured with an outer coating formulated to undergo timed degradation in vivo. The outer coating is composed of biocompatible polymers selected to control the rate of degradation and the lifespan of the optical fiber according to its intended purpose. For example optical fibers may serve as tissue-embedded sensors or in situ laser power sources that function for hours, days, weeks, months or years prior to biodegradation.

A biodegradable optical fiber is constructed from polymers that undergo hydrolysis in vivo and are biocompatible. For example, cellulose butyrate and hydroxypropyl cellulose can be incorporated into an optical fiber preform (i.e., precursor) and drawn into optical fibers after heating the preform to approximately 180° C. Fibers with transparency windows (i.e., light transmission wavelengths) of 700 nm-1100 nm may be obtained (see e.g., Dupuis et al., *Optics Letters* 32: 109-111, 2007 which is incorporated herein by reference). Manufacture of biocompatible optical fibers from cellulose esters, e.g., cellulose butyrate and hydroxypropyl cellulose, is described. For example, optical fibers may be manufactured with a core diameter of 10 μm and a cladding diameter of 50 μm with transparencies between wavelengths of 0.4 μm and 1.1 μm. See e.g., U.S. Pat. No. 8,553,223 issued to McKenna on Oct. 8, 2013, which is incorporated herein by reference. Optical fibers composed of cellulose derivatives may be rapidly hydrolyzed when exposed to tissues and fluids, especially in an acidic environment. Rapidly degrading optical fibers are coated with biocompatible polymers that degrade more slowly to control the lifespan of the fibers.

Optical fibers are composed of an inner core and an outer cladding that are rapidly degraded in vivo. The optical fibers may be coated in a biodegradable coating. The biodegradable coating degrades at a rate selected for the specific application. For example, an implanted optic fiber for sensing a biomarker of disease may be useful for 6 months or more to monitor an outpatient. Alternatively, a relatively short-lived optical fiber may be needed to monitor an internal wound and thus it may be coated with polymers known to degrade approximately 4 weeks after implantation, and an optic fiber for irradiation of tumor cells in situ may be coated with polymers that degrade after several weeks of tumor irradiation. Biocompatible polymer compositions may degrade in days, weeks, months or years. See e.g., Babak Ghanbarzadeh and Hadi Almasi (2013), *Biodegradable Polymers, Biodegradation—Life of Science*, Dr.

Rolando Chamy (Ed.), ISBN: 978-953-51-1154-2, InTech, DOI: 10.5772/56230 which is incorporated herein by reference.

For example, cellulose fibers degrade rapidly in situ, while cellulose derivatives, e.g. esters and ethers, are more durable with lifespans in weeks and months. Biodegradation rates of cellulose esters depend on the degree of esterification. Specific adducts to cellulose, e.g., hydroxypropyl methyl cellulose, cellulose acetate, and cellulose butyrate differ in their biodegradation times. See e.g., Ghanbarzadeh and Almasi, Ibid. Other polymers may be used to coat the optic fibers and control their rate of biodegradation in vivo. For example, amylose, amylopectin, starch, lignins, pectins, chitin, chitosan, poly (lactide) and poly (glycolide) may be used to create coatings that are stable to degradation for days or up to years. For example, biodegradable polyesters tailored for controlled degradation may be synthesized from glycolide and lactide with degradation times ranging in weeks to months. See e.g., Mader, Biodegradable Polymers Info Sheet available online at: http://www.sigmaaldrich-.com/technical-documents/articles/material-matters/re-somer-biodegradeable-polymers.html which is incorporated herein by reference. Optical fiber coatings are applied during the drawing process and degradable coatings of variable composition and different thickness are incorporated by surrounding the optical fiber. See e.g., U.S. Pat. No. 6,400,880 issued to Hebert et al. on Jun. 4, 2002 and U.S. Pat. No. 8,369,673 issued to Hawkes et al. on Feb. 5, 2013 which are incorporated herein by reference.

Prophetic Example 2: A Photodegradable Optical Fiber for Tissue Implantation

A biodegradable optical fiber for medical implantation is manufactured with a photodegradable outer layer coating that degrades when irradiated with UV light. Photodegradation of the outer layer coating exposes the optic fiber to tissues and fluids that will biodegrade the optic fiber. Photodegradable optical fibers may be used as: 1) light-based sensors of chemicals and cells; 2) conduits for light transmission to organs, tissues and cells, (e.g., optogenetics), and 3) directed sources of irradiation to ablate tumor cells, bacteria and other targets. The implanted photodegradable optical fiber may be degraded in situ at any time by irradiating the photodegradable outer layer coating and initiating photo-degradation and bio-degradation of the optical fiber.

A degradable optical fiber is constructed with multiple biodegradable channels and a photodegradable outer layer coating. An optical fiber with two concentric channels is constructed from polymers which biodegrade rapidly when exposed to physiological fluids. The manufacture and composition of multichannel optical fibers are described (see e.g., U.S. Pat. No. 8,553,223 Ibid.). For example the optic fiber may have an inner channel consisting of a polymeric core and cladding, composed of polylactic acid (or polyglycolic acid) which biodegrade rapidly when exposed to tissues and physiological fluids. See e.g., Babak Ghanbarzadeh and Hadi Almasi, Ibid. A concentric outer channel is constructed with UV transparent polymers to leak UV light externally, i.e. radially, from the optic fiber. The outer channel is a lossy UV fiber with a very thin cladding, approximately 1 micron thick, which allows UV radiation (approximately 300 nm wavelength) to leak as evanescent waves that penetrate the cladding and escape from the fiber. See e.g., U.S. Pat. No. 6,835,679 issued to Bilanin et al. on Dec. 28, 2004, which is incorporated herein by reference. A photodegradable outer layer coating surrounds the outer cladding and protects the optic fiber from biodegradation. The photodegradable outer layer coating is composed of a mixture of a base polymer and a photodegradable ketocarbonyl containing polymer. For example, a copolymer of styrene (95 wt %) and methylisopentylketone (5 wt %) may be used to coat the optic fiber. See e.g., U.S. Patent Appl. No. 2010/0249912 by Gibbons, Jr. et al. published on Sep. 30, 2010, which is incorporated herein by reference. Irradiation of the copolymer coating with UV light results in cleavage of chemical bonds in the ketocarbonyl polymer and degradation of the coating. The thickness and composition of the outer coating can be modified to control the rate of photodegradation and the required UV irradiation. For example, the photodegradable copolymer may contain about 0.01 wt % to about 10 wt % ketocarbonyl groups to alter the rate of degradation.

The photodegradable fiber optic is empowered with multiple light sources to drive the inner channel, e.g. a sensor, and the outer channel to initiate photodegradation. Fiber optic connectors link the light sources to the outer and inner channels. Fiber optic connectors for lasers, laser diodes and LEDs may be used. See e.g., U.S. Pat. No. 8,553,223 Ibid. Light sources for the fiber optics may be argon ion lasers that emit at 13 wavelengths through the visible, ultraviolet, and near-visible spectrum, wavelengths including: 351.1 nm, 363.8 nm, 454.6 nm, 457.9 nm, 465.8 nm, 476.5 nm, 488.0 nm, 496.5 nm, 501.7 nm, 514.5 nm, 528.7 nm, 1092.3 nm. See e.g., Wikipedia article: "List of laser types" available online at: http://en.wikipedia.org/wiki/List_of_laser_types which is incorporated herein by reference. Alternatively laser diodes that emit at wavelengths between 266 nm and 1940 nm may be connected to the channels of the optical fiber. Laser diodes are available from Lasermate Group, Inc., Walnut, Calif.; see attached sheet: Laser Diode Modules. For example, a laser diode emitting UV light at 266 nm may be connected to the outer channel of the optical fiber, and a laser diode emitting near infrared light at 760 nm may be connected to the inner channel for sensing oxygen saturation. See e.g., Kreeger et al., Ann. Thoracic Surg. 94: 1527-33, 2012, which is incorporated herein by reference.

To initiate photodegradation of the optical fiber a healthcare worker or a user signals control circuitry to activate the UV laser diode to emit UV light that is transmitted down the outer channel of the optical fiber. The UV light in the outer channel leaks through the outer cladding and initiates photodegradation of the outer coating. Once the implanted biodegradable optical fiber is exposed to physiological fluids rapid biodegradation occurs. The inner channel of the degradable optical fiber may function as a sensor to monitor: body temperature, blood pressure, blood flow, heart rate; or physiological levels of biochemical, e.g., pH, pO2, glucose, enzymes, antibodies, antigens. Alternatively, the optical fiber may deliver light for: imaging, optogenetics, photodynamic therapy or tissue ablation. See e.g., the article: "Medical Applications of Fiber Optics" by Alex Mendez which is available online at: http://www.laserfocusworld.com/articles/2011/01/medical-applications-of-fiber-optics-optical-fiber-sees-growth-as-medical-sensors.html and Bernstein and Boyden, Trends in Cognitive Sciences 15: 592-600, 2011, which are incorporated herein by reference.

Prophetic Example 3: A Photodegradable Optical Fiber for Tissue Implantation

A biodegradable optical fiber for medical implantation is manufactured with a photodegradable optical fiber, including a biodegradable optically functional inner fiber including an optically-transmitting cladding in contact with and surrounding an optically-transmitting core. The photodegradable optical fiber degrades when irradiated with UV light. Photo-degradation of the optical fiber exposes the optically-transmitting cladding and the optically-transmitting core to tissues and fluids that will further biodegrade the optical fiber. Photodegradable optical fibers may be used as: 1) light-based sensors of chemicals and cells; 2) conduits for light transmission to organs, tissues and cells, (e.g., optogenetics), and 3) directed sources of irradiation to ablate tumor cells, bacteria and other targets. The implanted photodegradable optical fiber may be degraded in situ at any time by irradiating the photodegradable optical fiber and initiating photo-degradation and bio-degradation of the optical fiber. For functional use of the optic fiber, transmissions between approximately 400 nm to 750 nm may be used to empower sensors, deliver light for imaging, and other biomedical applications. Photodegradation of the optically-transmitting cladding surrounding an optically-transmitting core may be initiated by irradiation with 300 nm wavelength light.

A photodegradable optical fiber is composed of a combination of plastic polymers. PMMA (acrylic) may be the core material, and fluorinated polymers are the cladding material. A higher-performance photodegradable optical fiber is based on perfluorinated polymers (mainly polyperfluorobutenylvinylether). In larger-diameter fibers, 96% of the cross section is the core that allows the transmission of light. The core size of photodegradable optical fiber composed of plastic polymers is in some cases 100 times larger than the core size of glass fiber.

Polymer-based biodegradable optical fibers have been developed as microstructured polymer optical fibers (mPOF), a type of photonic crystal fiber. mPOF fiber has applications that apply to biological sensing. Single and multimode POF may be used advantageously over using silica fiber, since the POF can be stretched further without breaking.

Some general properties of plastic polymer optical fibers are: (1) PMMA and Polystyrene are used as fiber core, with refractive indices of 1.49 and 1.59 respectively. (2) Generally, fiber cladding is made of silicone resin (refractive index ~1.46). (3) High refractive index difference is maintained between core and cladding. (4) High numerical aperture. (5) Have high mechanical flexibility and low cost. (6) Attenuation loss is about 1 dB/m @ 650 nm. (7) Bandwidth is ~5 MHz-km @ 650 nm.

The photodegradable optical fiber may be composed of a condensation copolymer in combination with a UV photodegradable ketocarbonyl-containing copolymer, e.g., $R_1(CO)R_2$. The condensation polymer may include a vinylidene monomer which is compatible with the ketocarbonyl groups. A minor proportion of a UV photodegradable copolymer may be combined based upon one of the monomers of the condensation copolymer. For example, UV photodegradable copolymer may be a composition combining polymethylmethacrylate (major proportion) and ketocarbonyl containing copolymers of methylmethacrylate (minor proportion).

An optically functional inner fiber including an optically-transmitting cladding in contact with and surrounding an optically-transmitting core may be constructed with an optically-transmitting core composed of 95 wt % polymethylmethacrylate and 5 wt % ketocarbonyl methylmethacrylate that will photodegrade when irradiated with UV light, e.g., approximately 300 nm wavelength light. An optically-transmitting cladding may be composed of a perfluorinated polymer that is mixed with a keto-carbonyl analogue copolymer. For example, the cladding may be composed of a copolymer of 95 wt % perfluorobutenylvinylether and 5 wt % keto-carbonyl perfluorobutenylvinylether. Photodegradation of the optically-transmitting cladding surrounding an optically-transmitting core may be initiated by irradiation with 300 nm wavelength light. See e.g., Gibbons Jr. et al. U.S. 2010/0249912, which is incorporated herein by reference.

For functional use of the optic fiber, transmissions between approximately 400 nm to 750 nm may be used to empower sensors, deliver light for imaging, and other biomedical applications. Optical plastic materials and their properties, including Spectral Passing Band, Refractive Index and Transmittance are chosen. Optical plastic materials are chosen depending upon the desired optical, physical, environmental, chemical and manufacturing properties. Optical plastic materials are chosen from acrylic (PMMA), polystyrene, polycarbonate, NAS, polyolefin, Arton F, optores (OZ1000-1100) or optores (OZ1310-1330). See, e.g., Info Sheet: "Properties of Plastic Materials" Align Optics, Sunrise, Fla. available online at http://www.plasticoptics.com/optical-plastic-materials.html, which is incorporated herein by reference.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will recognize that there are various vehicles by which processes and/or systems and/or other technologies disclosed herein can be effected (e.g., hardware, software, and/or firmware), and that the preferred vehicle will vary with the context in which the processes and/or systems and/or other technologies are deployed. For example, if a surgeon determines that speed and accuracy are paramount, the surgeon may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies disclosed herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those having ordinary skill in the art will recognize that optical aspects of implementations will typically employ optically-oriented hardware, software, and or firmware.

In a general sense the various aspects disclosed herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices disclosed herein, or a microdigital processing unit configured by a computer program which at least partially carries out processes and/or devices disclosed herein), electrical circuitry forming a memory device (e.g., forms of random access memory), and/or electrical circuitry forming a communications device (e.g., a modem, communications switch, or optical-electrical equipment). The subject matter disclosed herein may be implemented in an analog or digital fashion or some combination thereof.

In an embodiment, the system and the device are integrated in such a manner that the system operates as a unique system configured specifically for function of the biodegradable optical fiber device or the photodegradable optical fiber device, and any associated computing devices of the system operate as specific use computers for purposes of the claimed system or claimed device, and not general use computers. In an embodiment, at least one associated computing device of the system operates as specific use computers for purposes of the claimed system, and not general use computers. In an embodiment, at least one of the associated computing devices of the system are hardwired with a specific ROM to instruct the at least one computing device. In an embodiment, one of skill in the art recognizes that the biodegradable optical fiber device, the photodegradable optical fiber device, and associated system effect an improvement at least in the technological fields of biomedical therapeutics, biomedical diagnostics, or surgery.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device comprising:
a degradable optical fiber including
a biodegradable optically functional inner fiber formed from one or more degradable polymer types responsive to physiological fluid, the biodegradable optically functional inner fiber including an optically-transmitting cladding in contact with and surrounding an optically-transmitting core, wherein at least the optically-transmitting cladding is formed from a UV transparent polymer and configured to radially leak UV radiation out of the optically-transmitting cladding; and
a photodegradable outer layer in contact with and surrounding the optically-transmitting cladding of the biodegradable optically functional inner fiber to form a protective coating, wherein the photodegradable outer layer is formed from a photodegradable material responsive to the radially leaked UV radiation from the optically-transmitting cladding.

2. The device of claim 1, wherein the photodegradable outer layer is less optically transmissive than the cladding or the core.

3. The device of claim 1, wherein the photodegradable outer layer has an index of refraction greater than an index of refraction of the cladding.

4. The device of claim 1, wherein the biodegradable optically functional inner fiber formed from the one or more degradable polymer types responsive to physiological fluid and including the optically-transmitting cladding in contact with and surrounding the optically-transmitting core is biodegradable on a substantially instantaneous time scale.

5. A method for treating a vertebrate subject comprising:
propagating a first defined wavelength of electromagnetic radiation axially along a degradable optical fiber inserted into the vertebrate subject to treat a disease or condition, the degradable optical fiber including a biodegradable inner fiber in contact with and surrounded by a photodegradable outer layer, the biodegradable inner fiber formed from one or more degradable polymer types responsive to physiological fluid and including an optically-transmitting cladding in contact with and surrounding an optically-transmitting core, wherein the optically-transmitting cladding is formed from a UV transparent polymer and configured to radially leak UV radiation out of the optically-transmitting cladding, and the photodegradable outer layer in contact with and surrounding the optically-transmitting cladding of the biodegradable inner fiber to form a protective coating, wherein the photodegradable outer layer is formed from a photodegradable material responsive to the radially leaked UV radiation from the optically-transmitting cladding; and
propagating UV radiation axially along the degradable optical fiber inserted into the vertebrate subject, wherein the UV radiation degrades the photodegradable outer layer of the degradable optical fiber.

6. The method of claim 5, comprising propagating the first defined wavelength of electromagnetic radiation axially along the degradable optical fiber inserted into the vertebrate subject to treat the disease or condition in combination with administering a pharmaceutical composition.

7. The method of claim 5, comprising inserting the device comprising the degradable optical fiber into a blood vessel or lymph vessel of the vertebrate subject and propagating the first defined wavelength of electromagnetic radiation axially along the degradable optical fiber to induce relaxation or dilation of a blood vessel wall or a lymph vessel wall.

8. The method of claim 5, comprising propagating electromagnetic radiation of a wavelength of 440 to 470 nanometers axially along the degradable optical fiber inserted in the vertebrate subject to treat the disease or condition.

9. A device comprising:
a dual-channel degradable optical fiber including:
a biodegradable inner channel formed from one or more degradable polymer types responsive to physiological fluid, the biodegradable inner channel including an optically-transmitting inner cladding in contact with and surrounding an optically-transmitting inner core, wherein the biodegradable inner channel is configured to axially transmit a defined wavelength of electromagnetic radiation as part of a physiological sensor;
a biodegradable outer channel in contact with and surrounding the biodegradable inner channel, wherein the biodegradable outer channel is configured to axially transmit UV radiation, and wherein the biodegradable outer channel is formed from a biodegradable UV transparent polymer response to the physiological fluid and including an optically-transmitting outer core in contact with and surrounded by a thin layer of optically-transmitting outer cladding, the optically-transmitting outer cladding configured to radially leak the axially transmitted UV radiation; and
a photodegradable outer layer in contact with and surrounding the optically-transmitting outer cladding of the biodegradable outer channel to form a protective coating around at least a portion of the dual-channel degradable optical fiber, wherein the photodegradable outer layer is formed from a photodegradable material responsive to the radially leaked UV radiation from the optically-transmitting outer cladding.

* * * * *